(12) United States Patent
Pages et al.

(10) Patent No.: US 10,047,156 B2
(45) Date of Patent: Aug. 14, 2018

(54) ANTI-CXCL1, CXCL7 AND CXCL8 ANTIBODIES AND THEIR APPLICATIONS

(71) Applicants: Centre National De La Recherche Scientifique, Paris (FR); Universite de Nice Sophia Antipolis, Nice (FR)

(72) Inventors: Gilles Pages, Monaco (MC); Renaud Grepin, Merignac (FR)

(73) Assignees: Centre National De La Recherche Scientifique (CNRS) (FR); Universite de Nice Sophia Antipolis (FR)

( * ) Notice: Subject to any disclaimer, the term of this patent is extended or adjusted under 35 U.S.C. 154(b) by 89 days.

(21) Appl. No.: 14/891,833

(22) PCT Filed: May 19, 2014

(86) PCT No.: PCT/EP2014/060201
§ 371 (c)(1),
(2) Date: Nov. 17, 2015

(87) PCT Pub. No.: WO2014/184384
PCT Pub. Date: Nov. 20, 2014

(65) Prior Publication Data
US 2016/0108117 A1    Apr. 21, 2016

(30) Foreign Application Priority Data
May 17, 2013  (EP) .................................... 13305642

(51) Int. Cl.
| C07K 16/24 | (2006.01) |
| C07H 21/04 | (2006.01) |
| C12N 15/00 | (2006.01) |
| G01N 33/68 | (2006.01) |

(52) U.S. Cl.
CPC ............ *C07K 16/24* (2013.01); *C07K 16/244* (2013.01); *G01N 33/6863* (2013.01); *G01N 33/6893* (2013.01); *C07K 2317/33* (2013.01); *C07K 2317/34* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 4,676,980 A | 6/1987 | Segal et al. |
| 4,816,397 A | 3/1989 | Boss et al. |
| 4,816,567 A | 3/1989 | Cabilly et al. |
| 4,946,778 A | 8/1990 | Ladner et al. |
| 5,223,409 A | 6/1993 | Ladner et al. |
| 6,121,424 A | 9/2000 | Whitlow et al. |

FOREIGN PATENT DOCUMENTS

| WO | 91/17271 A1 | 11/1991 |
| WO | 92/18619 A1 | 10/1992 |
| WO | 2006/074179 A2 | 7/2006 |
| WO | 2008/130969 A2 | 10/2008 |
| WO | 2011/100271 A2 | 8/2011 |

OTHER PUBLICATIONS

Rudikoff et al Proc Natl Acad Sci USA 79: 1979-1983 (1982).*
Colman Research in Immunology 145: 33-36, (1994).*
Kussie et al. J. Immunol. 152: 146-152, (1994).*
Chen et al. EMBO J., 14: 2784-2794, (1995).*
International Search Report issued from corresponding PCT/EP2014/060201, dated Jul. 30, 2014.
Addison C et al.: 11 The CXC Chemokine Receptor 2. CXCR2. Is the putative Receptor for ELR+ CXC Chemokine-Induced Angiogenic Activity~. The Journal of Immunology. The American Association of Immunologists. US. vol. 165. Jan. 1, 2000 (Jan. 1, 2000). pp. 5269-5277. XP008122757. ISSN: 0022-1767 p. 5274.
Auerbach et al., Regional Differences in the Incidence and Growth of Mouse Tumors Following Intradermal or Subcutaneous Inoculation, Cancer Research, vol. 38, 1978, pp. 1739-1744.
Bourcier et al., Constitutive ERK Activity Induces Downregulation of Tristetraprolin, a Major Protein Controlling Interleukin8/CXCL8 mRNA Stability in Melanoma Cells, American Physiological Society-Cell Physiology, vol. 301, Sep. 2011, pp. 609-618.
Carmeliet et al., Angiogenesis in Cancer and Other Diseases, Nature, vol. 407, Sep. 14, 2000, pp. 249-257.
Chothia et al., Canonical Structures for the Hypervariable Regions of Immunoglobulins, J. Mol. Biology, 196, 1987, pp. 901-917.
Chothia et al., Conformations of Immunoglobulin Hypervariable Regions, Nature, vol. 342, Dec. 21-28, 1989, pp. 877-883.
Choueiri et al., Efficacy of Sunitinib and Sorafenib in Metastatic Papillary and Chromophobe Renal Cell Carcinoma, Journal of Clinical Oncology, vol. 26, No. 1, Jan. 1, 2008, pp. 127-131.
Cole et al., The EBV—Hybridoma Technique, Methods Enzymology, vol. 121, 1986, pp. 140-167.
Ebos et al., Accelerated Metasis After Short-Term Treatment With a Potent Inhibitor of Tumor Andiogenesis, Cancer Cell, Mar. 3, 2009, pp. 232-239.
Eisen et al., Sorafenib for Older Patients With Renal Cell Carcinoma: Subset Analysis From a Randomized Trial, J Natl Cancer Inst, vol. 100, Issue 20, Oct. 15, 2008, pp. 1454-1563.

(Continued)

*Primary Examiner* — Vanessa L. Ford
*Assistant Examiner* — Jegatheesan Seharaseyon
(74) *Attorney, Agent, or Firm* — Banner & Witcoff, Ltd.

(57) ABSTRACT

The invention provides an isolated antibody or a fragment thereof, which is directed to the human chemokines CXCL1, CXCL7 and CXCL8, said antibody or fragment being capable of binding to the human chemokine CXCL1 with an equilibrium dissociation constant ($K_D$) of at most 16 nM, to the human chemokine CXCL7 with an equilibrium dissociation constant ($K_D$) of at most 5 nM and to the human chemokine CXCL8 with an equilibrium dissociation constant ($K_D$) of at most 45 nM, as determined by surface plasmon resonance. The invention also provides some applications of said isolated antibody.

10 Claims, 9 Drawing Sheets

(56) References Cited

OTHER PUBLICATIONS

Escudier et al., Phase III Trial of Bevacizumab Plus Interferon Alfa-2a in Patients With Metastatic Renal Cell Carcinoma (avoren): Final Analysis of Overall Survival, Journal of Clinical Oncology, vol. 28, No. 13, May 1, 2010, pp. 2144-2150.
Grepin et al., Acceleration of Clear Cell Renal Cell Carcinoma Growth in Mice Following Bevacizumab/Avastin Treatment: The Role of CXCL Cytokines, Oncogene, 31, 2012, pp. 1683-1694.
Harper et al., VEGF-A Splicing: The Key to Anti-Angiogenic Therapeutics? Nat Rev Cancer, 8(11), 2008, pp. 880-887.
Hurwitz et al., Bevacizumab plus Irinotecan, Fluorouracil, and Leucovorin for Metastatic Colorectal Cancer, The New England Journal of Medicine, vol. 350, No. 23, Jun. 3, 2004, pp. 2335-2342.
Huse et al., Generation of a Large Combination Library of the Immunoglobulin Repertoire in Phage Lambda, Science, vol. 246, Dec. 8, 1989, pp. 1275-1281.
J Katancik: "Interleukin 8. Neutrophil-Activating Peptide-2 and GRO-[alpha] Bind to and Elicit Cell Activation via Specific and Different Amino Acid Residues of CXCR2", Cytokine. vol. 12. No. 10. Oct. 1, 2000 (Oct. 1, 2000). pp. 1480-1488. XP055078150. ISSN: 1043-4666. DOI: 10.1006jcyto.2000.0742 the whole document.
Kozbor et al., The Production of Monoclonal Antibodies from Human Lymphocytes, Immunology Today, vol. 4, No. 3, 1983, pp. 72-79.
Köhler et al., Continuous Cultures of Fused Cells Secreting Antibody of Predefined Specificity, Nature, vol. 256, Aug. 7, 1975, pp. 495-497, Nov. 6, 2017.
Motzer et al., Efficacy of Everolimus in Advanced Renal Cell Carcinoma: A Double-Blind, Randomised, Placebo-Controlled Phase III Trial, Lancet, vol. 372, Aug. 9, 2008, pp. 449-456.
Paez et al., Antiangiogenic Therapy Elicits Malignant Progression of Tumors to Increased Local Invasion and Distant Metastasis, Cancer Cell, 15(3), Mar. 3, 2009, pp. 220-231.
Sambrook et al., Molecular Cloning a Laboratory Manual, Second Edition, Cold Spring Harbor Laboratory, 1989, pp. 9.47-9.55.
Yao et al., Interleukin-8 Modulates Growth and Invasiveness of Estrogen Receptor-Negative Breast Cancer Cells, Int. J. Cancer, 121, 2007, pp. 1949-1957.

\* cited by examiner

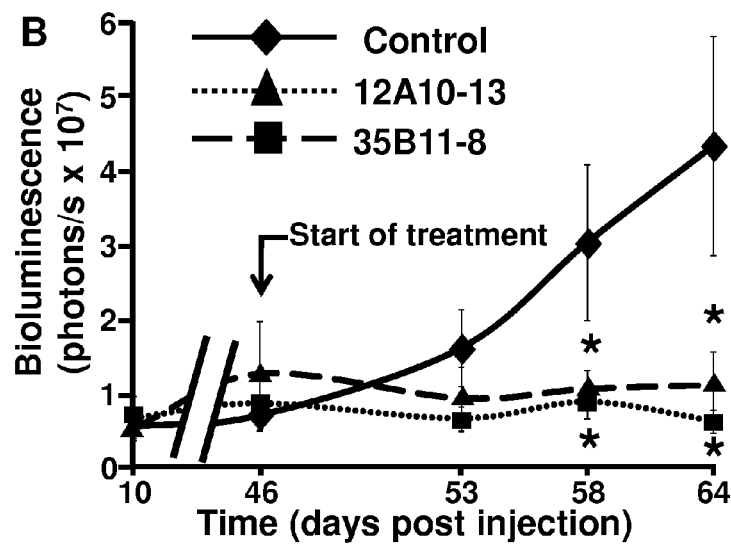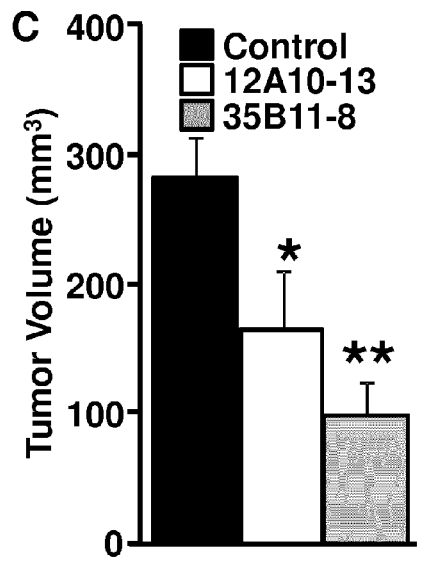
FIGURE 1

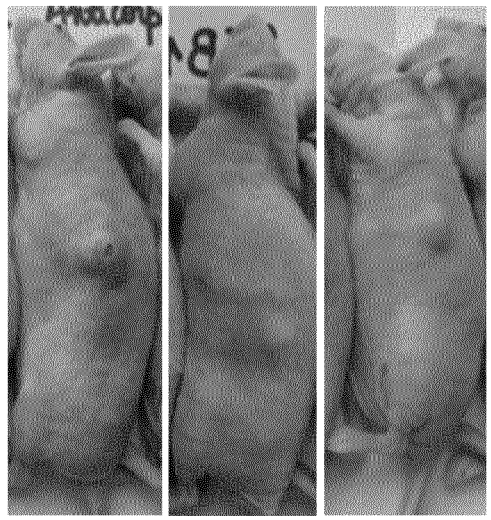
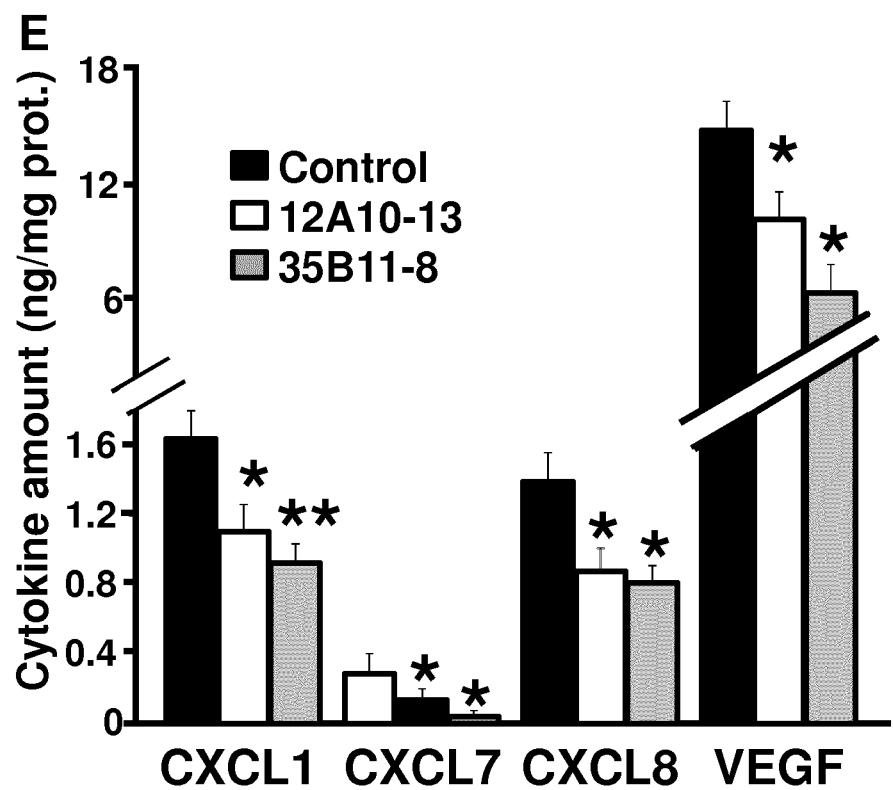
FIGURE 1

| Kd (nM)  | CXCL1 | CXCL3 | CXCL7 | CXCL8 |
|----------|-------|-------|-------|-------|
| 12A10-13 | 15.6  | 64.5  | 3.3   | 44.3  |
| 35B11-8  | 11.8  | 247   | 4.99  | 19.9  |
| Kd (nM)  | CXCL1 | CXCL3 | CXCL7 | CXCL8 |
|----------|-------|-------|-------|-------|
| AC 1     | 5.48  |       |       |       |
| AC 1,2,3 | 15.3  | 29.2  |       |       |
| AC 7     |       |       | 7.3   |       |
| AC 8     |       |       |       | 20.4  |
| Ka (x M10Exp8) | CXCL1 | CXCL3 | CXCL7 | CXCL8 |
|----------------|-------|-------|-------|-------|
| 12A10-13       | 63,9  | 15,5  | 3.03  | 22.6  |
| 35B11-8        | 84,7  | 404   | 2.01  | 50.3  |
| Ka (x M10Exp8) | CXCL1 | CXCL3 | CXCL7 | CXCL8 |
|----------------|-------|-------|-------|-------|
| AC 1           | 1.82  |       |       |       |
| AC 1,2,3       | 65.36 | 34.2  |       |       |
| AC 7           |       |       | 1.37  |       |
| AC 8           |       |       |       | 49    |
FIGURE 4
*Antibodies 35B11-8* : IgG1
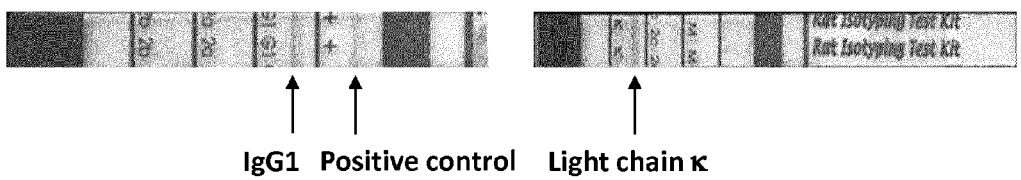
↑ ↑      ↑
IgG1 Positive control    Light chain κ
*Antibodies12A10-13* : IgG2c
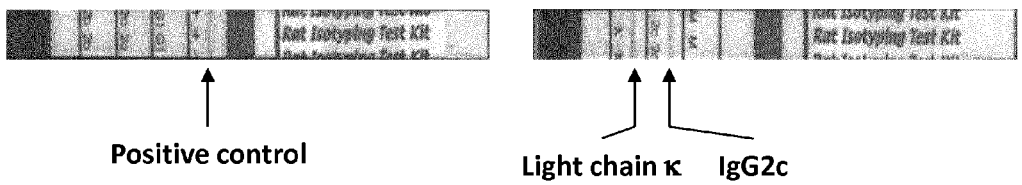
↑      ↑ ↑
Positive control    Light chain κ    IgG2c
FIGURE 5

| Variable<br>Clinical parameters | Description | HR [95%CI] | Log-Rank |
|---|---|---|---|
| Age | Per year | 1.03 [0.97-1.1] | 0.29 |
| Sex | Male | 1 | 0.33 |
|  | Female | 0.55 [0.16-1.9] | - |
| Previous Cancer | No | 1 | 0.61 |
|  | Yes | 1.50 [0.33-6.4] | - |
| Metastasis at diagnosis | No | 1 | $<10^{-3}$ |
|  | Yes | 6.4 [2.5-17] | - |
| Fuhrman stage (group) | 1/2 | 1 | 0.001 |
|  | 3/4 | 7.80 [1.8-34] | - |
| Biological parameters |  |  |  |
| VEGF (V-Vb) | Per Unit | 1 [0.99-1] | 0.26 |
| CXCL1 | Per Unit | 2.47 [1.17-5.22] | 0.017 |
| CXCL7 | Per Unit | 20.20 [3.12-130.5] | 0.0015 |
| CXCL8 | Per unit | 1.15 [0.77-1.68] | 0.49 |

FIGURE 7

| Variable<br>Clinical parameters | Description | HR [95%CI] | Log-Rank |
|---|---|---|---|
| Metastasis at diagnosis | No | 1 | 0.0005 |
|  | Yes | 8.09 [2.52-26] | - |
| Fuhrman stage (group) | 1/2 | 1 | 0.007 |
|  | 3/4 | 7.84 [1.74-35.18] | - |
| Biological parameters |  |  |  |
| CXCL1 | Per Unit | 2.34 [0.97-5.7] | 0.059 |
| CXCL7 | Per Unit | 8.46 [1.53-46.62] | 0.014 |

FIGURE 8

```
                        SEQUENCE LISTING

<160> NUMBER OF SEQ ID NOS: 24

<210> SEQ ID NO 1
<211> LENGTH: 11
<212> TYPE: PRT
<213> ORGANISM: Artificial sequence
<220> FEATURE:
<223> OTHER INFORMATION: Light chain CDR1 (LC-CDR1) - hybridoma 35B11-8

<400> SEQUENCE: 1

Gln Ala Ser Gln Asn Ile Asn Lys Tyr Ile Ala
1               5                   10

<210> SEQ ID NO 2
<211> LENGTH: 6
<212> TYPE: PRT
<213> ORGANISM: Artificial sequence
<220> FEATURE:
<223> OTHER INFORMATION: Light chain CDR2 (LC-CDR2) - hybridoma 35B11-8

<400> SEQUENCE: 2

Thr Ser Thr Leu Val Ser
1               5

<210> SEQ ID NO 3
<211> LENGTH: 9
<212> TYPE: PRT
<213> ORGANISM: Artificial sequence
<220> FEATURE:
<223> OTHER INFORMATION: Light chain CDR3 (LC-CDR3) - hybridoma 35B11-8

<400> SEQUENCE: 3

Leu Gln Tyr Asp Asn Ser Pro Phe Pro
1               5

<210> SEQ ID NO 4
<211> LENGTH: 9
<212> TYPE: PRT
<213> ORGANISM: Artificial sequence
<220> FEATURE:
<223> OTHER INFORMATION: Heavy chain CDR1 (HC-CDR1) - hybridoma 35B11-8

<400> SEQUENCE: 4

Gly Phe Thr Phe Asn Asn Tyr Trp Met
1               5

<210> SEQ ID NO 5
<211> LENGTH: 17
<212> TYPE: PRT
<213> ORGANISM: Artificial sequence
<220> FEATURE:
<223> OTHER INFORMATION: Heavy chain CDR2 (HC-CDR2) - hybridoma 35B11-8

<400> SEQUENCE: 5

Ser Ile Ser Lys Thr Gly Ser Asn Pro Tyr Tyr Pro Asp Ser Val Lys
1               5                   10                  15

Gly

<210> SEQ ID NO 6
```

```
<211> LENGTH: 14
<212> TYPE: PRT
<213> ORGANISM: Artificial sequence
<220> FEATURE:
<223> OTHER INFORMATION: Heavy chain CDR3 (HC-CDR3) - hybridoma 35B11-8

<400> SEQUENCE: 6

Asp Gly Thr Thr Pro Leu Asp Tyr Trp Gly Gln Gly Val Met
1               5                   10

<210> SEQ ID NO 7
<211> LENGTH: 10
<212> TYPE: PRT
<213> ORGANISM: Artificial sequence
<220> FEATURE:
<223> OTHER INFORMATION: Light chain CDR1 (LC-CDR1) - hybridoma 12A10-13

<400> SEQUENCE: 7

Arg Ala Ser Ser Ser Val Ser Tyr Met His
1               5                   10

<210> SEQ ID NO 8
<211> LENGTH: 6
<212> TYPE: PRT
<213> ORGANISM: Artificial sequence
<220> FEATURE:
<223> OTHER INFORMATION: Light chain CDR2 (LC-CDR2) - hybridoma 12A10-13

<400> SEQUENCE: 8

Thr Ser Lys Leu Ala Ser
1               5

<210> SEQ ID NO 9
<211> LENGTH: 9
<212> TYPE: PRT
<213> ORGANISM: Artificial sequence
<220> FEATURE:
<223> OTHER INFORMATION: Light chain CDR3 (LC-CDR3) - hybridoma 12A10-13

<400> SEQUENCE: 9

Gln Gln Trp Ser Ser Asn Ser Leu Thr
1               5

<210> SEQ ID NO 10
<211> LENGTH: 9
<212> TYPE: PRT
<213> ORGANISM: Artificial sequence
<220> FEATURE:
<223> OTHER INFORMATION: Heavy chain CDR1 (HC-CDR1) - hybridoma 12A10-13

<400> SEQUENCE: 10

Gly Tyr Thr Phe Thr Ser Tyr Tyr Ile
1               5

<210> SEQ ID NO 11
<211> LENGTH: 17
<212> TYPE: PRT
<213> ORGANISM: Artificial sequence
<220> FEATURE:
<223> OTHER INFORMATION: Heavy chain CDR2 (HC-CDR2) - hybridoma 12A10-13

<400> SEQUENCE: 11

Tyr Ile Asn Thr Gly Ser Gly Gly Thr Asn Tyr Asn Glu Lys Phe Lys
1               5                   10                  15

Gly
```

```
<210> SEQ ID NO 12
<211> LENGTH: 13
<212> TYPE: PRT
<213> ORGANISM: Artificial sequence
<220> FEATURE:
<223> OTHER INFORMATION: Heavy chain CDR3 (HC-CDR3) - hybridoma 12A10-13

<400> SEQUENCE: 12

Pro Ser Gly Gly Phe Asp Tyr Trp Gly Gln Gly Val Met
1               5                   10

<210> SEQ ID NO 13
<211> LENGTH: 107
<212> TYPE: PRT
<213> ORGANISM: Artificial sequence
<220> FEATURE:
<223> OTHER INFORMATION: Light chain (LC) - hybridoma 35B11-8

<400> SEQUENCE: 13

Asp Ile Gln Met Thr Gln Ser Pro Ser Leu Ser Ala Ser Leu Gly
1               5                   10                  15

Asp Lys Val Thr Ile Thr Cys Gln Ala Ser Gln Asn Ile Asn Lys Tyr
                20                  25                  30

Ile Ala Trp Tyr Gln Gln Lys Pro Gly Lys Ala Pro Gly Leu Leu Ile
            35                  40                  45

His Tyr Thr Ser Thr Leu Val Ser Gly Ile Pro Ser Arg Phe Ser Gly
    50                  55                  60

Ser Gly Ser Gly Arg Val Tyr Ser Phe Ser Ile Ser Asn Val Glu Ser
65                  70                  75                  80

Glu Asp Ile Ala Ser Tyr Tyr Cys Leu Gln Tyr Asp Asn Ser Pro Phe
                85                  90                  95

Pro Phe Gly Ala Gly Thr Lys Leu Glu Leu Lys
            100                 105

<210> SEQ ID NO 14
<211> LENGTH: 117
<212> TYPE: PRT
<213> ORGANISM: Artificial sequence
<220> FEATURE:
<223> OTHER INFORMATION: Heavy chain (HC) - hybridoma 35B11-8

<400> SEQUENCE: 14

Glu Val Gln Leu Val Glu Ser Gly Gly Leu Val Gln Pro Gly Arg
1               5                   10                  15

Ser Leu Lys Leu Ser Cys Val Ala Ser Gly Phe Thr Phe Asn Asn Tyr
                20                  25                  30

Trp Met Thr Trp Ile Arg Gln Ala Pro Gly Lys Gly Leu Glu Trp Val
            35                  40                  45

Ala Ser Ile Ser Lys Thr Gly Ser Asn Pro Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ser Glu Asp Thr Ala Thr Tyr Tyr Cys
                85                  90                  95

Ala Arg Asp Gly Thr Thr Pro Leu Asp Tyr Trp Gly Gln Gly Val Met
            100                 105                 110

Val Thr Val Ser Ser
        115

<210> SEQ ID NO 15
```

```
<211> LENGTH: 106
<212> TYPE: PRT
<213> ORGANISM: Artificial sequence
<220> FEATURE:
<223> OTHER INFORMATION: Light chain (LC) - hybridoma 12A10-13

<400> SEQUENCE: 15

Glu Ile Val Leu Thr Gln Ser Pro Thr Thr Met Ala Ala Ser Pro Gly
1               5                   10                  15

Glu Lys Val Thr Ile Thr Cys Arg Ala Ser Ser Ser Val Ser Tyr Met
            20                  25                  30

His Trp Tyr Gln Gln Lys Pro Gly Ala Ser Pro Lys Pro Trp Ile Tyr
        35                  40                  45

Asp Thr Ser Lys Leu Ala Ser Gly Val Pro Asn Arg Phe Ser Gly Ser
    50                  55                  60

Gly Ser Gly Thr Ser Tyr Ser Leu Thr Ile Ser Ser Met Glu Thr Glu
65                  70                  75                  80

Asp Thr Ala Thr Tyr Tyr Cys Gln Gln Trp Ser Ser Asn Ser Leu Thr
                85                  90                  95

Phe Gly Ser Gly Thr Lys Leu Glu Ile Lys
            100                 105

<210> SEQ ID NO 16
<211> LENGTH: 117
<212> TYPE: PRT
<213> ORGANISM: Artificial sequence
<220> FEATURE:
<223> OTHER INFORMATION: Heavy chain (HC) - hybridoma 12A10-13

<400> SEQUENCE: 16

Gln Val Gln Leu Gln Gln Ser Gly Ala Glu Leu Ala Lys Pro Gly Ser
1               5                   10                  15

Ser Val Lys Ile Ser Cys Lys Ala Ser Gly Tyr Thr Phe Thr Ser Tyr
            20                  25                  30

Tyr Ile Ser Trp Ile Lys Gln Thr Thr Gly Gln Gly Leu Glu Tyr Ile
        35                  40                  45

Gly Tyr Ile Asn Thr Gly Ser Gly Gly Thr Asn Tyr Asn Glu Lys Phe
    50                  55                  60

Lys Gly Lys Ala Thr Leu Thr Val Asp Lys Ser Ser Ser Thr Ala Phe
65                  70                  75                  80

Met Gln Leu Ser Ser Leu Thr Pro Asp Asp Ser Ala Val Tyr Tyr Cys
                85                  90                  95

Ala Ser Pro Ser Gly Gly Phe Asp Tyr Trp Gly Gln Gly Val Met Val
            100                 105                 110

Thr Val Ser Ser Ala
        115

<210> SEQ ID NO 17
<211> LENGTH: 1184
<212> TYPE: DNA
<213> ORGANISM: Homo sapiens
<220> FEATURE:
<221> NAME/KEY: misc_feature
<223> OTHER INFORMATION: Human CXCL1

<400> SEQUENCE: 17
cacagagccc gggccgcagg cacctcctcg ccagctcttc cgctcctctc acagccgcca      60
gacccgcctg ctgagcccca tggccgcgcg tgctctctcc gccgccccca gcaatccccg     120
gctcctgcga gtggcactgc tgctcctgct cctggtagcc gctggccggc gcgcagcagg     180
```

```
agcgtccgtg gccactgaac tgcgctgcca gtgcttgcag accctgcagg gaattcaccc    240
caagaacatc caaagtgtga acgtgaagtc ccccggaccc cactgcgccc aaaccgaagt    300
catagccaca ctcaagaatg ggcggaaagc ttgcctcaat cctgcatccc ccatagttaa    360
gaaaatcatc gaaaagatgc tgaacagtga caaatccaac tgaccagaag ggaggaggaa    420
gctcactggt ggctgttcct gaaggaggcc ctgcccttat aggaacagaa gaggaaagag    480
agacacagct gcagaggcca cctggattgt gcctaatgtg tttgagcatc gcttaggaga    540
agtcttctat ttatttattt attcattagt tttgaagatt ctatgttaat attttaggtg    600
taaaataatt aagggtatga ttaactctac ctgcacactg tcctattata ttcattcttt    660
ttgaaatgtc aaccccaagt tagttcaatc tggattcata tttaatttga aggtagaatg    720
ttttcaaatg ttctccagtc attatgttaa tatttctgag gagcctgcaa catgccagcc    780
actgtgatag aggctggcgg atccaagcaa atggccaatg agatcattgt gaaggcaggg    840
gaatgtatgt gcacatctgt tttgtaactg tttagatgaa tgtcagttgt tatttattga    900
aatgatttca cagtgtgtgg tcaacatttc tcatgttgaa actttaagaa ctaaaatgtt    960
ctaaatatcc cttggacatt ttatgtcttt cttgtaaggc atactgcctt gtttaatggt   1020
agttttacag tgtttctggc ttagaacaaa ggggcttaat tattgatgtt tcatagaga    1080 atataaaaat aaagcactta tagaaaaaac tcgtttgatt tttgggggga aacaagggct   1140
acctttactg gaaaatctgg tgatttataa aaaaaaaaa aaaa                     1184

<210> SEQ ID NO 18
<211> LENGTH: 1307
<212> TYPE: DNA
<213> ORGANISM: Homo sapiens
<220> FEATURE:
<221> NAME/KEY: misc_feature
<223> OTHER INFORMATION: Human CXCL7

<400> SEQUENCE: 18
acttatctgc agacttgtag gcagcaactc accctcactc agaggtcttc tggttctgga     60
aacaactcta gctcagcctt ctccaccatg agcctcagac ttgataccac cccttcctgt    120
aacagtgcga gaccacttca tgccttgcag gtgctgctgc ttctgtcatt gctgctgact    180
gctctggctt cctccaccaa aggacaaact aagagaaact ggcgaaagg caaagaggaa    240 agtctagaca gtgacttgta tgctgaactc cgctgcatgt gtataaagac aacctctgga    300
attcatccca aaaacatcca aagtttggaa gtgatcggga aggaaccca ttgcaaccaa    360 gtcgaagtga tagccacact gaaggatggg aggaaaatct gcctggaccc agatgctccc    420
agaatcaaga aaattgtaca gaaaaaattg gcaggtgatg aatctgctga ttaatttgtt    480
ctgtttctgc caaacttctt taactcccag gaagggtaga attttgaaac cttgattttc    540
tagagttctc atttattcag gatacctatt cttactgtat taaaatttgg atatgtgttt    600
cattctgtct caaaaatcac atttatttct gagaaggttg gttaaaagat ggcagaaaga    660
agatgaaaat aaataagcct ggtttcaacc ctctaattct tgcctaaaca ttggactgta    720
ctttgcattt ttttcttta aaatttctat tctaacacaa cttggttgat ttttcctggt    780
ctactttatg gttattagac atactcatgg gtattattag atttcataat ggtcaatgat    840
aataggaatt acatggagcc caacagagaa tatttgctca atacattttt gttaatatat    900
ttaggaactt aatggagtct ctcagtgtct tagtcctagg atgtcttatt taaaatactc    960
cctgaaagtt tattctgatg tttatttag ccatcaaaca ctaaaataat aaattggtga   1020
```

| | |
|---|---|
| atatgaatct tataaactgt ggttagctgg tttaaagtga atatatttgc cactagtaga | 1080 |
| acaaaaatag atgatgaaaa tgaattaaca tatctacata gttataattc tatcattaga | 1140 |
| atgagcctta taaataagta caatatagga cttcaacctt actagactcc taattctaaa | 1200 |
| ttctactttt ttcatcaaca gaactttcat tcatttttta aaccctaaaa cttatacccca | 1260 |
| cactattctt acaaaaatat tcacatgaaa taaaaatttg ctattga | 1307 |

<210> SEQ ID NO 19
<211> LENGTH: 1718
<212> TYPE: DNA
<213> ORGANISM: Homo sapiens
<220> FEATURE:
<221> NAME/KEY: misc_feature
<223> OTHER INFORMATION: Human CXCL8

<400> SEQUENCE: 19

| | |
|---|---|
| gagggtgcat aagttctcta gtagggtgat gatataaaaa gccaccggag cactccataa | 60 |
| ggcacaaact ttcagagaca gcagagcaca caagcttcta ggacaagagc caggaagaaa | 120 |
| ccaccggaag gaaccatctc actgtgtgta aacatgactt ccaagctggc cgtggctctc | 180 |
| ttggcagcct tcctgatttc tgcagctctg tgtgaaggtg cagttttgcc aaggagtgct | 240 |
| aaagaactta gatgtcagtg cataaagaca tactccaaac cttccacccc caaatttatc | 300 |
| aaagaactga gagtgattga gagtggacca cactgcgcca acacagaaat tattgtaaag | 360 |
| ctttctgatg aagagagct ctgtctggac cccaaggaaa actgggtgca gagggttgtg | 420 |
| gagaagtttt tgaagagggc tgagaattca taaaaaaatt cattctctgt ggtatccaag | 480 |
| aatcagtgaa gatgccagtg aaacttcaag caaatctact tcaacacttc atgtattgtg | 540 |
| tgggtctgtt gtagggttgc cagatgcaat acaagattcc tggttaaatt tgaatttcag | 600 |
| taaacaatga atagttttc attgtaccat gaaatatcca gaacatactt atatgtaaag | 660 |
| tattatttat ttgaatctac aaaaaacaac aaataatttt taaatataag gattttccta | 720 |
| gatattgcac gggagaatat acaaatagca aaattgaggc caagggccaa gagaatatcc | 780 |
| gaactttaat ttcaggaatt gaatgggttt gctagaatgt gatatttgaa gcatcacata | 840 |
| aaaatgatgg gacaataaat tttgccataa agtcaaattt agctggaaat cctggatttt | 900 |
| tttctgttaa atctggcaac cctagtctgc tagccaggat ccacaagtcc ttgttccact | 960 |
| gtgccttggt ttctccttta tttctaagtg gaaaaagtat tagccaccat cttacctcac | 1020 |
| agtgatgttg tgaggacatg tggaagcact ttaagttttt tcatcataac ataaattatt | 1080 |
| ttcaagtgta acttattaac ctatttatta tttatgtatt tatttaagca tcaaatattt | 1140 |
| gtgcaagaat ttggaaaaat agaagatgaa tcattgattg aatagttata agatgttat | 1200 |
| agtaaattta ttttatttta gatattaaat gatgtttat tagataaatt tcaatcaggg | 1260 |
| ttttttagatt aaacaaacaa acaattgggt acccagttaa attttcattt cagataaaca | 1320 |
| acaaataatt tttagtata agtacattat tgtttatctg aaattttaat tgaactaaca | 1380 |
| atcctagttt gatactccca gtcttgtcat tgccagctgt gttggtagtg ctgtgttgaa | 1440 |
| ttacggaata atgagttaga actattaaaa cagccaaaac tccacagtca atattagtaa | 1500 |
| tttcttgctg gttgaaactt gtttattatg tacaaataga ttcttataat attatttaaa | 1560 |
| tgactgcatt tttaaataca aggctttata ttttttaactt taagatgttt ttatgtgctc | 1620 |
| tccaaatttt tttttactgtt tctgattgta tggaaatata aagtaaaata tgaaacattt | 1680 |
| aaaatataat ttgttgtcaa agtaaaaaaa aaaaaaaa | 1718 |

<210> SEQ ID NO 20
<211> LENGTH: 25
<212> TYPE: PRT
<213> ORGANISM: Artificial sequence
<220> FEATURE:
<223> OTHER INFORMATION: pCXCL7

<400> SEQUENCE: 20

Ser Asp Leu Tyr Ala Glu Leu Arg Cys Met Cys Ile Lys Thr Thr Ser
1               5                   10                  15

Gly Ile His Pro Lys Asn Ile Gln Ser
            20                  25

<210> SEQ ID NO 21
<211> LENGTH: 25
<212> TYPE: PRT
<213> ORGANISM: Artificial sequence
<220> FEATURE:
<223> OTHER INFORMATION: pCXCL1

<400> SEQUENCE: 21

Ala Ser Val Ala Thr Glu Leu Arg Cys Gln Cys Leu Gln Thr Leu Gln
1               5                   10                  15

Gly Ile His Pro Lys Asn Ile Gln Ser
            20                  25

<210> SEQ ID NO 22
<211> LENGTH: 25
<212> TYPE: PRT
<213> ORGANISM: Artificial sequence
<220> FEATURE:
<223> OTHER INFORMATION: pCXCL2

<400> SEQUENCE: 22

Ala Pro Leu Ala Thr Glu Leu Arg Cys Gln Cys Leu Gln Thr Leu Gln
1               5                   10                  15

Gly Ile His Leu Lys Asn Ile Gln Ser
            20                  25

<210> SEQ ID NO 23
<211> LENGTH: 25
<212> TYPE: PRT
<213> ORGANISM: Artificial sequence
<220> FEATURE:
<223> OTHER INFORMATION: pCXCL3

<400> SEQUENCE: 23

Ala Ser Val Val Thr Glu Leu Arg Cys Gln Cys Leu Gln Thr Leu Gln
1               5                   10                  15

Gly Ile His Leu Lys Asn Ile Gln Ser
            20                  25

<210> SEQ ID NO 24
<211> LENGTH: 26
<212> TYPE: PRT
<213> ORGANISM: Artificial sequence
<220> FEATURE:
<223> OTHER INFORMATION: pCXCL8

-continued

<400> SEQUENCE: 24

Pro Arg Ser Ala Lys Glu Leu Arg Cys Gln Cys Ile Lys Thr Tyr Ser
1               5                   10                  15

Lys Pro Phe His Pro Lys Phe Ile Lys Glu
                20              25

ANTI-CXCL1, CXCL7 AND CXCL8 ANTIBODIES AND THEIR APPLICATIONS

The present invention relates to the field of prevention and treatment of diseases related to the chemokines CXCL1, CXCL7 and CXCL8, particularly of pathological angiogenesis diseases.

In particular, the invention relates to antibodies directed to the chemokines CXCL1, CXCL7 and CXCL8 and their applications, particularly for use as a medicament for the treatment and/or prevention of diseases related to the chemokines CXCL1, CXCL7 and CXCL8, notably pathological angiogenesis diseases.

Targeting angiogenesis for treating cancer was proposed by Judah Folkman in the early 1970s. This initial hypothesis was validated by numerous pre-clinical and clinical studies and has resulted in the development of many therapeutic compounds including humanized monoclonal antibodies and large spectrum of kinase inhibitors.

One of the most important factors of angiogenesis is the VEGF (Vascular Endothelial Growth Factor). Almost twenty years after the discovery of VEGF, bevacizumab (Hurwitz et al., 2004), a humanized monoclonal antibody targeting VEGF, obtained Food and Drug Agency (FDA) approval for treating colon cancers in association with a standard chemotherapeutic agent irinotecan.

Other numerous anti-angiogenic compounds have also been developed including receptor tyrosine kinase inhibitors, like sunitinib malate (Choueiri et al., 2008) and sorafenib tosylate (Eisen et al., 2008) but also inhibitors of intracellular kinase like temsirolimus (Motzer et al., 2008) and non-receptor serine threonine kinase inhibitors.

Despite significant increase in progression free survival using these therapies, inevitable relapse and disease progression to death was observed. Some recent papers describe a new phenomenon called treatment evasion and the selection of more aggressive cells with increased metastasis potential in the case of treatment with tyrosine kinase inhibitors (Ebos et al., 2009, Paez-Ribes et al., 2009).

In this way, VEGF has been targeted for RCC antiangiogenic therapy; however targeting VEGF alone has been only partially successful. Despite significant increase in progression free survival using the neutralizing humanized antibody to VEGF (i.e. Bevacizumab), (Yang et al., 2003) (Escudier et al., NEJM 2007), no significant differences in overall survival between placebo and Bevacizumab treated patients were reported in the pivotal AVOREN study presented at the ASCO meeting 2009 (Escudier et al., 2010). Evasion of treatment could arise via different mechanisms including angiogenic redundancy or inefficacy due to the presence of anti-angiogenic forms of VEGF called VEGFxxxb, resulting from an alternative splicing of VEGF pre mRNA (Harper, 2008).

WO 2008/130969 discloses monoclonal antibodies obtained by the injection into a mouse of a mixture of said five antigens, said antibodies being able to bind to five antigens: human IL-8 (CXCL8), Gro-alpha (CXCL1), Gro-beta (CXCL2), Gro-gamma (CXCL3) and ENA-78 (CXCL5), and discloses the use of said antibodies in an inhaled LPS acute lung inflammatory model in non-human primates. However, WO 2008/130969 does not disclose a monoclonal antibody binding to CXCL1, CXCL7 and CXCL8.

WO 2011/100271 discloses monoclonal antibodies able to bind to human IL-8 (CXCL8), Gro-alpha (CXCL1), Gro-beta (CXCL2), Gro-gamma (CXCL3), GCP2, NAP2 (CXCL7) and ENA-78 (CXCL5). However, WO 2011/100271 does not disclose the affinity of said monoclonal antibodies for said antigens.

There remains therefore a significant need in the art for new and improved anti-angiogenic compounds that increase patients' lifespan and avoid relapse and disease progression to death. The present inventors have made a significant step forward with the invention disclosed herein.

The purpose of the invention is to fulfill this need by providing new compounds, which make it possible to solve in whole or part the problems mentioned-above.

Unexpectedly, the inventors have demonstrated that their newly developed antibodies directed to the chemokines CXCL1, CXCL7 and CXCL8 are able to inhibit efficiently tumor growth, in particular in a mouse model of RCC (Clear cell renal cell carcinoma). RCC is one of the most relevant models for the study of anti-angiogenic therapies, since RCC are highly vascularized tumors (that arise due to mutations in the von Hippel Lindau gene).

These results are unexpected, since several recent papers describe that suppression of chemokines, including CXCL8, does not inhibit but on the contrary promotes tumor growth. In this way, Yao et al. (2007) have demonstrated that suppression of CXCL-8 promoted tumor growth in nude mice.

Surprisingly, these newly developed antibodies are able to inhibit tumor growth more efficiently than commercial anti-CXCL1, anti-CXCL7 and anti-CXCL8 antibodies used alone or in combination. These results are really surprising since the inventors have demonstrated that the combination of commercial anti-CXCL7 and anti-CXCL8 antibodies (with or without commercial anti-CXCL1 antibodies) does not able to obtain an additive effect on the inhibition of tumor growth. On the contrary, the inventors have shown that the combined use of commercial anti-CXCL7 and anti-CXCL8 antibodies is less efficient than their separate use on the inhibition of tumor growth and has a pro-tumoral effect in a mouse model of RCC.

Thus, in one aspect, the invention relates to an isolated antibody or a fragment thereof, which is directed to the human chemokines CXCL1, CXCL7 and CXCL8, said antibody or fragment thereof being capable of binding to the human chemokine CXCL1 with an equilibrium dissociation constant ($K_D$) of at most 16 nM, to the human chemokine CXCL7 with an equilibrium dissociation constant ($K_D$) of at most 5 nM and to the human chemokine CXCL8 with an equilibrium dissociation constant ($K_D$) of at most 45 nM as determined by surface plasmon resonance, particularly at 25° C. and more particularly according to the plasmon resonance analysis, sold under the trademark Biacore® Plasmon resonance analysis described in the examples.

The antibody of the invention can be obtained by immunizing animals, like rats, with peptides specific for human CXCL7 but sharing similarities with human CXCL1 and 8, particularly with the peptide of sequence SDLYAELRCM-CIKTTSGIHPKNIQS (SEQ ID NO: 20) following by screening methods to isolate antibody. Different screening methods to isolate antibody can be used including ELISA tests on said peptide coupled to keyhole limpet hemocyanine and tests of the capacity of antibodies to inhibit CXCL-7 induced ERK activation in cells expressing CXCR2 as described in Bourcier et al. (2011).

In a particular embodiment, the present invention also relates to an antibody obtained by, or susceptible to be obtained by, a method comprising the following steps:
  i) immunizing at least an animal with at least one peptide specific for human CXCL7 but sharing similarities with human CXCL1 and 8, and in particular with a peptide of sequence SDLYAELRCMCIKTTSGIHPKNIQS (SEQ ID NO: 20),
ii) generating monoclonal antibodies by any method known by a man skilled in the art, such as isolating B cells from said animal and fusing said B cells with myeloma cells to form immortal hybridoma cells that are able to secrete monoclonal antibodies,
iii) performing screening methods to isolate an antibody able to bind to a peptide of sequence SEQ ID NO: 20, or to a peptide of sequence SEQ ID NO: 20 coupled to keyhole limpet hemocyanin, and/or an antibody able to inhibit CXCL-7 induced ERK activation in cells expressing CXCR2, in particular in an assay as described in Bourcier et al. (2011).

The antibodies according to the invention have in particular the following advantages:

They are unique described antibodies directed to multiple CXCL chemokines, in particular CXCL1, CXCL7 and CXCL8;

Their affinity for each chemokine CXCL1, CXCL7 and CXCL8 is important compared to commercially available ones directed against only one of said chemokines;

Compared to Bevacizumab (antibody directed to VEGF) which increases tumor growth in experimental models (Escudier et al., 2010), the antibodies of the invention inhibit tumors growth;

The antibodies of the invention target an independent angiogenic pathway different of the classical VEGF/VEGFR pathway. The CXCL chemokine pathway is both angiogenic and inflammatory. Moreover CXCL chemokines induce an autocrine proliferation pathway because tumor cells express their receptors CXCR1 and CXCR2. Hence by inhibiting relevant CXCL chemokines (CXCL1, CXCL7 and CXCL8) angiogenesis, inflammation and proliferation is inhibited by the antibodies of the invention.

Unless defined otherwise, all technical and scientific terms used herein have the same meaning as commonly understood to one skilled in the relevant art.

For convenience, the meaning of certain term and phrases employed in the specification and claims are provided.

The term "antibody" as used herein is intended to include monoclonal antibodies, polyclonal antibodies, multispecific antibodies (e.g. bispecific antibodies). More particularly, an antibody (or "immunoglobulin") consists of a glycoprotein comprising at least two heavy (H) chains and two light (L) chains inter-connected by disulfide bonds.

Each heavy chain comprises a heavy chain variable region (or domain) (abbreviated herein as $V_H$) and a heavy chain constant region (hereafter $C_H$). Heavy chains are classified as gamma, mu, alpha, delta, or epsilon, and define the antibody's isotype as IgG, IgM, IgA, IgD, and IgE, respectively. The heavy chain constant region of the immunoglobulin IgG, IgD, and IgA ($\gamma$, $\delta$ and $\alpha$ chains respectively) comprises three domains (CH1, CH2, and CH3) and a hinge region for added flexibility, and the heavy chain constant region of the immunoglobulin IgM and IgE contains 4 domains (CH1, CH2, CH3, and CH4).

The antibody of the invention can be of the IgG, IgM, IgA, IgD, and IgE isotype, depending on the structure of its heavy chain. However, in a preferred embodiment, the antibody of the invention is of the IgG isotype, i.e., its heavy chain is of the gamma ($\gamma$) type.

IgG antibodies are classified in four distinct subtypes, named IgG1, IgG2, IgG3 and IgG4 in order of their abundance in serum (IgG1 being the most abundant). The structure of the hinge regions in the $\gamma$ chain gives each of these subtypes its unique biological profile (even though there is about 95% similarity between their Fc regions, the structure of the hinge regions is relatively different).

The antibody of the invention can be of the IgG1, IgG2, IgG3 or IgG4 subtype.

However, in a preferred embodiment, the antibody of the invention is of the IgG1 subtype or of the IgG2 subtype.

Each light chain comprises a light chain variable region (abbreviated herein as $V_L$) and a light chain constant region comprising only one domain, $C_L$. There are two types of light chain in mammals: the kappa ($\kappa$) chain, encoded by the immunoglobulin kappa locus on chromosome 2, and the lambda ($\lambda$) chain, encoded by the immunoglobulin lambda locus on chromosome 22. In a preferred embodiment, the antibody of the invention has a Kappa light chain.

The $V_H$ and $V_L$ regions can be further subdivided into regions of hypervariability, termed "Complementarity Determining Regions" (CDR), which are primarily responsible for binding an epitope of an antigen, and which are interspersed with regions that are more conserved, termed "Framework Regions" (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The assignment of amino acid sequences to each domain is in accordance with well-known conventions (CHOTHIA et al., *J. Mol. Biol.*, 1987; CHOTHIA et al., *Nature*, 1989). The functional ability of the antibody to bind a particular antigen depends on the variable regions of each light/heavy chain pair, and is largely determined by the CDRs. The variable region of the heavy chain differs in antibodies produced by different B cells, but is the same for all antibodies produced by a single B cell or B cell clone (or hybridome).

By contrast, the constant regions of the antibodies mediate the binding of the immunoglobulin to host tissues or factors, including various cells of the immune system (e.g. effector cells) and the first component (Clq) of the classical complement system.

As used herein, the term "antibody fragments" intends to designate Fab, Fab', F(ab')2, scFv, dsFv, ds-scFv, dimers, minibodies, diabodies, and multimers thereof and bispecific antibody fragments so long as they exhibit the desired biological activities (i.e. they are directed to the chemokines CXCL1, CXCL7 and CXCL8). Antibodies can be fragmented using conventional techniques. Various techniques have been developed for the production of antibody fragments. Traditionally, these fragments were derived via proteolytic digestion of intact antibodies. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be synthesized by recombinant techniques.

In the context of the present invention, an antibody is said to "be directed to" or "bind" a peptide if said antibody has an affinity constant $K_a$ (which is the inverted equilibrium dissociation constant, i.e. $1/K_D$) higher than $10^7 M^{-1}$, preferably higher than $5.10^7 M^{-1}$, more preferably higher than $10^8 M^{-1}$ for said peptide.

The affinity constant which is used to characterize the binding of antibodies (Ab) to a peptide or an antigen (Ag) is the inverted dissociation constant defined as follows:

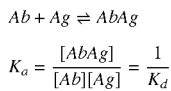

$$Ab + Ag \rightleftharpoons AbAg$$
$$K_a = \frac{[AbAg]}{[Ab][Ag]} = \frac{1}{K_d}$$

This affinity can be measured for example by equilibrium dialysis, by fluorescence quenching or by surface plasmon resonance, these technologies being routinely used in the art. In particular, the equilibrium dissociation constant ($K_D$) and the affinity constant ($K_a$) can be determined by surface plasmon resonance according to the method described in the examples.

Particularly, the isolated antibody or a fragment thereof of the invention is being capable of binding to the human chemokine CXCL1 with an equilibrium dissociation constant ($K_D$) of at most 16 nM, to the human chemokine CXCL7 with an equilibrium dissociation constant ($K_D$) of at most 4 nM and to the human chemokine CXCL8 with an equilibrium dissociation constant ($K_D$) of at most 45 nM as determined by surface plasmon resonance, particularly at 25° C. and more particularly according to the plasmon resonance analysis, sold under the trademark BIACORE®Plasmon resonance analysis described in the examples.

Particularly, the isolated antibody or a fragment thereof of the invention is being capable of binding to the human chemokine CXCL1 with an equilibrium dissociation constant ($K_D$) of at most 12 nM, to the human chemokine CXCL7 with an equilibrium dissociation constant ($K_D$) of at most 5 nM and to the human chemokine CXCL8 with an equilibrium dissociation constant ($K_D$) of at most 20 nM as determined by surface plasmon resonance, particularly at 25° C. and more particularly according to the plasmon resonance analysis, sold under the trademark BIACORE®Plasmon resonance analysis described in the examples.

As used herein, the term "CXCL1" relates to the CXC chemokine also known as growth-regulated oncogene alpha, GRO-α.

Preferably, human CXCL1 relates to the chemokine encoded by the sequence set forth in SEQ ID NO: 17. (NCBI Reference Sequence: NM_001511).

As used herein, the term "CXCL7" relates to the CXC chemokine also known as Neutrophil Activating Peptide-2, NAP-2.

Preferably, human CXCL7 relates to the chemokine encoded by the sequence set forth in SEQ ID NO: 18. (GenBank: NM_002704).

As used herein, the term "CXCL8" relates to the CXC chemokine also known as Interleukin 8, IL-8.

Preferably, human CXCL8 relates to the chemokine encoded by the sequence set forth in SEQ ID NO: 19 (GenBank: NM_000584).

The percentages of identity to which reference is made in the presentation of the present invention are determined on the basis of a global alignment of sequences to be compared, that is to say, on an alignment of sequences over their Gentire length, using for example the algorithm of Needleman and Wunsch 1970. This sequence comparison can be done for example using the needle software by using the parameter "Gap open" equal to 10.0, the parameter "Gap Extend" equal to 0.5, and a matrix "BLOSUM 62". Software such as needle is available on the website ebi.ac.uk worldwide, under the name "needle".

In particular, the isolated antibody or a fragment thereof, which is directed to the human chemokines CXCL1, CXCL7 and CXCL8, according to the invention comprises at least one, in particular at least two, at least three, at least four, at least five and more particularly six Complementary Determining Regions (CDRs) chosen among the CDRs of sequence comprising or consisting of SEQ ID No: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 1 over the entire length of SEQ ID NO: 1, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 2 over the entire length of SEQ ID NO: 2, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 3 over the entire length of SEQ ID NO: 3, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 4 over the entire length of SEQ ID NO: 4, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 5 over the entire length of SEQ ID NO: 5, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 6 over the entire length of SEQ ID NO: 6, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 7 over the entire length of SEQ ID NO: 7, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 8 over the entire length of SEQ ID NO: 8, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 9 over the entire length of SEQ ID NO: 9, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 10 over the entire length of SEQ ID NO: 10, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 11 over the entire length of SEQ ID NO: 11 or a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 12 over the entire length of SEQ ID NO: 12, in particular chosen among the CDRs of sequence consisting of SEQ ID No: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12.

Particularly, the isolated antibody or a fragment thereof, which is directed to the human chemokines CXCL1, CXCL7 and CXCL8, according to the invention comprises six Complementary Determining Regions (CDRs) selected from the group consisting of the CDRs of sequence selected from the group consisting of:

SEQ ID No: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, a sequence having at least 90% of identity with SEQ ID NO: 1 over the entire length of SEQ ID NO: 1, a sequence having at least 90% of identity with SEQ ID NO: 2 over the entire length of SEQ ID NO: 2, a sequence having at least 90% of identity with SEQ ID NO: 3 over the entire length of SEQ ID NO: 3, a sequence having at least 90% of identity with SEQ ID NO: 4 over the entire length of SEQ ID NO: 4, a sequence having at least 90% of identity with SEQ ID NO: 5 over the entire length of SEQ ID NO: 5, a sequence having at least 90% of identity with SEQ ID NO: 6 over the entire length of SEQ ID NO: 6, a sequence having at least 90% of identity with SEQ ID NO: 7 over the entire length of SEQ ID NO: 7, a sequence having at least 90% of identity with SEQ ID NO: 8 over the entire length of SEQ ID NO: 8, a sequence having at least 90% of identity with SEQ ID NO: 9 over the entire length of SEQ ID NO: 9, a sequence having at least 90% of identity with SEQ ID NO: 10 over the entire length of SEQ ID NO: 10, a sequence having at least 90% of identity with SEQ ID NO: 11 over the entire length of SEQ ID NO: 11, a sequence having at least 90% of identity with SEQ ID NO: 12 over the entire length of SEQ ID NO: 12, in particular SEQ ID No: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12.

Particularly, the isolated antibody or a fragment thereof, which is directed to the human chemokines CXCL1, CXCL7 and CXCL8, according to the invention comprises:

at least one, in particular at least two and more particularly three CDR(s) chosen among the CDRs of sequence comprising or consisting of SEQ ID No: 1, SEQ ID NO: 2, SEQ ID NO: 3, SEQ ID NO: 7, SEQ ID NO: 8, SEQ ID NO: 9, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 1 over the entire length of SEQ ID NO: 1, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 2 over the entire length of SEQ ID NO: 2, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 3 over the entire length of SEQ ID NO: 3, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 7 over the entire length of SEQ ID NO: 7, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 8 over the entire length of SEQ ID NO: 8 or a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 9 over the entire length of SEQ ID NO: 9, particularly chosen among the CDRs of sequence consisting of SEQ ID No: 1, SEQ ID NO: 2, SEQ ID NO: 3, SEQ ID NO: 7, SEQ ID NO: 8 or SEQ ID NO: 9; and at least one, in particular at least two and more particularly three CDR(s) chosen among the CDRs of sequence comprising or consisting of SEQ ID NO: 4, SEQ ID NO: 5, SEQ ID NO: 6, SEQ ID NO: 10, SEQ ID NO: 11, SEQ ID NO: 12, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 4 over the entire length of SEQ ID NO: 4, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 5 over the entire length of SEQ ID NO: 5, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 6 over the entire length of SEQ ID NO: 6, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 10 over the entire length of SEQ ID NO: 10, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 11 over the entire length of SEQ ID NO: 11 or a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 12 over the entire length of SEQ ID NO: 12, particularly chosen among the CDRs of sequence consisting of SEQ ID NO: 4, SEQ ID NO: 5, SEQ ID NO: 6, SEQ ID NO: 10, SEQ ID NO: 11 or SEQ ID NO: 12.

Particularly, the isolated antibody or a fragment thereof, which is directed to the human chemokines CXCL1, CXCL7 and CXCL8, according to the invention comprises:
  at least one, in particular at least two and more particularly three CDR(s) chosen among the CDRs of sequence comprising or consisting of SEQ ID No: 1, SEQ ID NO: 2, SEQ ID NO: 3, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 1 over the entire length of SEQ ID NO: 1, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 2 over the entire length of SEQ ID NO: 2, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 3 over the entire length of SEQ ID NO: 3, in particular chosen among the CDRs of sequence consisting of SEQ ID No: 1, SEQ ID NO: 2, SEQ ID NO: 3; or
  at least one, in particular at least two and more particularly three CDR(s) chosen among the CDRs of sequence comprising or consisting of SEQ ID No: 7, SEQ ID NO: 8, SEQ ID NO: 9, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 7 over the entire length of SEQ ID NO: 7, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 8 over the entire length of SEQ ID NO: 8 or a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 9 over the entire length of SEQ ID NO: 9, in particular chosen among the CDRs of sequence consisting of SEQ ID No: 7, SEQ ID NO: 8, SEQ ID NO: 9; and
  at least one, in particular at least two and more particularly three CDR(s) chosen among the CDRs of sequence comprising or consisting of SEQ ID NO: 4, SEQ ID NO: 5, SEQ ID NO: 6, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 4 over the entire length of SEQ ID NO: 4, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 5 over the entire length of SEQ ID NO: 5, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 6 over the entire length of SEQ ID NO: 6, in particular chosen among the CDRs of sequence consisting of SEQ ID NO: 4, SEQ ID NO: 5, SEQ ID NO: 6; or
  at least one, in particular at least two and more particularly three CDR(s) chosen among the CDRs of sequence comprising or consisting of SEQ ID NO: 10, SEQ ID NO: 11, SEQ ID NO: 12, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 10 over the entire length of SEQ ID NO: 10, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 11 over the entire length of SEQ ID NO: 11 or a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 12 over the entire length of SEQ ID NO: 12, in particular chosen among the CDRs of sequence consisting of SEQ ID NO: 10, SEQ ID NO: 11, SEQ ID NO: 12.

Particularly, the isolated antibody or a fragment thereof, which is directed to the human chemokines CXCL1, CXCL7 and CXCL8, according to the invention comprises:
  at least one, in particular at least two and more particularly three CDR(s) chosen among the CDRs of sequence comprising or consisting of SEQ ID No: 1, SEQ ID NO: 2, SEQ ID NO: 3, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 1 over the entire length of SEQ ID NO: 1, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 2 over the entire length of SEQ ID NO: 2, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 3 over the entire length of SEQ ID NO: 3, in particular chosen among the CDRs of sequence consisting of SEQ ID No: 1, SEQ ID NO: 2, SEQ ID NO: 3; and at least one, in particular at least two and more particularly three CDR(s) chosen among the CDRs of sequence comprising or consisting of SEQ ID NO: 4, SEQ ID NO: 5, SEQ ID NO: 6, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 4 over the entire length of SEQ ID NO: 4, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 5 over the entire length of SEQ ID NO: 5, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 6 over the entire length of SEQ ID NO: 6, in particular chosen among the CDRs of sequence consisting of SEQ ID NO: 4, SEQ ID NO: 5, SEQ ID NO: 6.

Particularly, the isolated antibody or a fragment thereof, which is directed to the human chemokines CXCL1, CXCL7 and CXCL8, according to the invention comprises:
at least one, in particular at least two and more particularly three CDR(s) chosen among the CDRs of sequence comprising or consisting of SEQ ID NO: 7, SEQ ID NO: 8, SEQ ID NO: 9, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 7 over the entire length of SEQ ID NO: 7, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 8 over the entire length of SEQ ID NO: 8 or a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 9 over the entire length of SEQ ID NO: 9, in particular chosen among the CDRs of sequence consisting of SEQ ID NO: 7, SEQ ID NO: 8, SEQ ID NO: 9; and
at least one, in particular at least two and more particularly three CDR(s) chosen among the CDRs of sequence comprising or consisting of SEQ ID NO: 10, SEQ ID NO: 11, SEQ ID NO: 12, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 10 over the entire length of SEQ ID NO: 10, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 11 over the entire length of SEQ ID NO: 11 or a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 12 over the entire length of SEQ ID NO: 12, in particular chosen among the CDRs of sequence consisting of SEQ ID NO: 10, SEQ ID NO: 11, SEQ ID NO: 12.

Particularly, the isolated antibody or a fragment thereof, which is directed to the human chemokines CXCL1, CXCL7 and CXCL8, according to the invention comprises six CDRs chosen among the CDRs of sequence comprising or consisting of SEQ ID No: 1, SEQ ID NO: 2, SEQ ID NO: 3, SEQ ID NO: 4, SEQ ID NO: 5, SEQ ID NO: 6, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 1 over the entire length of SEQ ID NO: 1, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 2 over the entire length of SEQ ID NO: 2, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 3 over the entire length of SEQ ID NO: 3, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 4 over the entire length of SEQ ID NO: 4, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 5 over the entire length of SEQ ID NO: 5, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 6 over the entire length of SEQ ID NO: 6, in particular chosen among the CDRs of sequence consisting of SEQ ID No: 1, SEQ ID NO: 2, SEQ ID NO: 3, SEQ ID NO: 4, SEQ ID NO: 5, SEQ ID NO: 6.

Particularly, the isolated antibody or a fragment thereof, which is directed to the human chemokines CXCL1, CXCL7 and CXCL8, according to the invention comprises six CDRs chosen among the CDRs of sequence comprising or consisting of SEQ ID NO: 7, SEQ ID NO: 8, SEQ ID NO: 9, SEQ ID NO: 10, SEQ ID NO: 11, SEQ ID NO: 12, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 7 over the entire length of SEQ ID NO: 7, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 8 over the entire length of SEQ ID NO: 8 or a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 9 over the entire length of SEQ ID NO: 9, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 10 over the entire length of SEQ ID NO: 10, a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 11 over the entire length of SEQ ID NO: 11 or a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 12 over the entire length of SEQ ID NO: 12, in particular chosen among the CDRs of sequence consisting of SEQ ID NO: 7, SEQ ID NO: 8, SEQ ID NO: 9, SEQ ID NO: 10, SEQ ID NO: 11, SEQ ID NO: 12.

In another embodiment of the antibody of the invention, the light chain variable region ($V_L$) comprises:
- a light chain CDR1 (LC-CDR1) of sequence SEQ ID NO: 1 or SEQ ID NO: 7 or of sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 1 over the entire length of SEQ ID NO: 1 or of sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 7 over the entire length of SEQ ID NO: 7, in particular of sequence SEQ ID NO: 1 or SEQ ID NO: 7; and/or
- a light chain CDR2 (LC-CDR2) of sequence SEQ ID NO: 2 or SEQ ID NO: 8 or of sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 2 over the entire length of SEQ ID NO: 2 or of sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 8 over the entire length of SEQ ID NO: 8, in particular of sequence SEQ ID NO: 2 or SEQ ID NO: 8; and/or
- a light chain CDR3 (LC-CDR3) of sequence SEQ ID NO: 3 or SEQ ID NO: 9 or of sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 3 over the entire length of SEQ ID NO: 3 or of sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 9 over the entire length of SEQ ID NO: 9, in particular of sequence SEQ ID NO: 3 or SEQ ID NO: 9; and wherein the heavy chain variable region (VH) comprises:
- a heavy chain CDR1 (HC-CDR1) of sequence SEQ ID NO: 4 or SEQ ID NO: 10 or of sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 4 over the entire length of SEQ ID NO: 4 or of sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 10 over the entire length of SEQ ID NO: 10, in particular of sequence SEQ ID NO: 4 or SEQ ID NO: 10; and/or
- a heavy chain CDR2 (HC-CDR2) of sequence SEQ ID NO: 5 or SEQ ID NO: 11 or of sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 5 over the entire length of SEQ ID NO: 5 or of sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 11 over the entire length of SEQ ID NO: 11, in particular of sequence SEQ ID NO: 5 or SEQ ID NO: 11; and/or
- a heavy chain CDR3 (HC-CDR3) of sequence SEQ ID NO: 6 or SEQ ID NO: 12 or of sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 6 over the entire length of SEQ ID NO: 6 or of sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 12 over the entire length of SEQ ID NO: 12, in particular of sequence SEQ ID NO: 6 or SEQ ID NO: 12.

In particular, the light chain variable region ($V_L$) of the antibody according to the invention comprises:
- a light chain CDR1 (LC-CDR1) of sequence SEQ ID NO: 1; and
- a light chain CDR2 (LC-CDR2) of sequence SEQ ID NO: 2; and
- a light chain CDR3 (LC-CDR3) of sequence SEQ ID NO: 3.

In particular, the heavy chain variable region ($V_H$) of the antibody according to the invention comprises:
- a heavy chain CDR1 (HC-CDR1) of sequence SEQ ID NO: 4; and
- a heavy chain CDR2 (HC-CDR2) of sequence SEQ ID NO: 5; and
- a heavy chain CDR3 (HC-CDR3) of sequence SEQ ID NO: 6.

In particular, the light chain variable region ($V_L$) of the antibody according to the invention comprises:
- a light chain CDR1 (LC-CDR1) of sequence SEQ ID NO: 7; and
- a light chain CDR2 (LC-CDR2) of sequence SEQ ID NO: 8; and
- a light chain CDR3 (LC-CDR3) of sequence SEQ ID NO: 9.

In particular, the heavy chain variable region ($V_H$) of the antibody according to the invention comprises:
- a heavy chain CDR1 (HC-CDR1) of sequence SEQ ID NO: 10; and
- a heavy chain CDR2 (HC-CDR2) of sequence SEQ ID NO: 11; and
- a heavy chain CDR3 (HC-CDR3) of sequence SEQ ID NO: 12.

In particular, the light chain variable region ($V_L$) of the antibody according to the invention comprises:
- a light chain CDR1 (LC-CDR1) of sequence SEQ ID NO: 1 or of sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 1 over the entire length of SEQ ID NO: 1, in particular of sequence SEQ ID NO: 1; and
- a light chain CDR2 (LC-CDR2) of sequence SEQ ID NO: 2 or of sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 2 over the entire length of SEQ ID NO: 2, in particular of sequence SEQ ID NO: 2; and
- a light chain CDR3 (LC-CDR3) of sequence SEQ ID NO: 3 or of sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 3 over the entire length of SEQ ID NO: 3, in particular of sequence SEQ ID NO: 3; and the heavy chain variable region (VH) comprises:
- a heavy chain CDR1 (HC-CDR1) of sequence SEQ ID NO: 4 or of sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 4 over the entire length of SEQ ID NO: 4, in particular of sequence SEQ ID NO: 4; and
- a heavy chain CDR2 (HC-CDR2) of sequence SEQ ID NO: 5 or of sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 5 over the entire length of SEQ ID NO: 5, in particular of sequence SEQ ID NO: 5; and
- a heavy chain CDR3 (HC-CDR3) of sequence SEQ ID NO: 6 or of sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 6 over the entire length of SEQ ID NO: 6, in particular of sequence SEQ ID NO: 6.

In particular, the light chain variable region ($V_L$) of the antibody according to the invention comprises:
- a light chain CDR1 (LC-CDR1) of sequence SEQ ID NO: 1; and
- a light chain CDR2 (LC-CDR2) of sequence SEQ ID NO: 2; and
- a light chain CDR3 (LC-CDR3) of sequence SEQ ID NO: 3; and the heavy chain variable region (VH) comprises:
- a heavy chain CDR1 (HC-CDR1) of sequence SEQ ID NO: 4; and
- a heavy chain CDR2 (HC-CDR2) of sequence SEQ ID NO: 5; and
- a heavy chain CDR3 (HC-CDR3) of sequence SEQ ID NO: 6.

In particular, the light chain variable region ($V_L$) of the antibody according to the invention comprises:
- a light chain CDR1 (LC-CDR1) of sequence SEQ ID NO: 7 or of sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 7 over the entire length of SEQ ID NO: 7, in particular of sequence SEQ ID NO: 7; and
- a light chain CDR2 (LC-CDR2) of sequence SEQ ID NO: 8 or of sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 8 over the entire length of SEQ ID NO: 8, in particular of sequence SEQ ID NO: 8; and
- a light chain CDR3 (LC-CDR3) of sequence SEQ ID NO: 9 or of sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 9 over the entire length of SEQ ID NO: 9, in particular of sequence SEQ ID NO: 9; and the heavy chain variable region (VH) comprises:
- a heavy chain CDR1 (HC-CDR1) of sequence SEQ ID NO: 10 or of sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 10 over the entire length of SEQ ID NO: 10, in particular of sequence SEQ ID NO: 10; and
- a heavy chain CDR2 (HC-CDR2) of sequence SEQ ID NO: 11 or of sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 11 over the entire length of SEQ ID NO: 11, in particular of sequence SEQ ID NO: 11; and
- a heavy chain CDR3 (HC-CDR3) of sequence SEQ ID NO: 12 or of sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 12 over the entire length of SEQ ID NO: 12, in particular of sequence SEQ ID NO: 12.

In particular, the light chain variable region ($V_L$) of the antibody according to the invention comprises:
- a light chain CDR1 (LC-CDR1) of sequence SEQ ID NO: 7; and
- a light chain CDR2 (LC-CDR2) of sequence SEQ ID NO: 8; and
- a light chain CDR3 (LC-CDR3) of sequence SEQ ID NO: 9; and the heavy chain variable region (VH) comprises:
- a heavy chain CDR1 (HC-CDR1) of sequence SEQ ID NO: 10; and
- a heavy chain CDR2 (HC-CDR2) of sequence SEQ ID NO: 11; and
- a heavy chain CDR3 (HC-CDR3) of sequence SEQ ID NO: 12.

In particular, the sequence of the light chain variable region ($V_L$) comprises or consists of the sequence SEQ ID NO: 13 or of a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 13 over the entire length of SEQ ID NO: 13 and/or the sequence of the heavy chain variable region ($V_H$) comprises or consists of the sequence SEQ ID NO: 14 or of a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 14 over the entire length of SEQ ID NO: 14.

In one embodiment, the sequence of the light chain variable region ($V_L$) consists of the sequence SEQ ID NO: 13 and the sequence of the heavy chain variable region ($V_H$) consists of the sequence SEQ ID NO: 14.

In particular, the sequence of the light chain variable region ($V_L$) comprises or consists of the sequence SEQ ID NO: 15 or of a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 15 over the entire length of SEQ ID NO: 15; and/or the sequence of the heavy chain variable region ($V_H$) comprises or consists of the sequence SEQ ID NO: 16 or of a sequence having at least 80%, in particular at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of identity with SEQ ID NO: 16 over the entire length of SEQ ID NO: 16.

In another embodiment, the sequence of the light chain variable region ($V_L$) consists of the sequence SEQ ID NO: 15 and the sequence of the heavy chain variable region ($V_H$) consists of the sequence SEQ ID NO: 16.

The antibody of the invention can be a polyclonal or a monoclonal antibody.

A "polyclonal antibody" as used herein, designates antibodies that are obtained from different B cell resources. It typically includes various antibodies directed against various determinants, or epitopes, of the target antigen(s). These antibodies may be produced in animals. Conventional techniques of molecular biology, microbiology and recombinant DNA techniques are within the skill of the art. Such techniques are explained fully in the literature. For example, the antibodies of the invention may be prepared by the following conventional method. A mammal (e.g. a mouse, hamster, or rabbit) can be immunized with an immunogenic form of CXCL1, CXCL7 and CXCL8, which elicit an antibody response in the mammal. Techniques for conferring immunogenicity on a polypeptide include conjugation to carriers or other techniques well known in the art. For example, the polypeptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

A "monoclonal antibody", as used herein, means an antibody arising from a nearly homogeneous antibody population. More particularly, the subject antibodies of a population are identical except for a few possible naturally-occurring mutations which can be found in minimal proportions. In other words, a monoclonal antibody consists of a homogeneous antibody arising from the growth of a single cell clone (for example a hybridoma, a eukaryotic host cell transfected with a DNA molecule coding for the homogeneous antibody, a prokaryotic host cell transfected with a DNA molecule coding for the homogeneous antibody, etc.) and is generally characterized by heavy chains of one and only one isotype and subtype, and light chains of only one type. In addition, in contrast with preparations of polyclonal antibodies, each monoclonal antibody is directed against a single epitope of an antigen.

To produce monoclonal antibodies, antibody producing cells (lymphocytes) can be harvested from the immunized animal as described above and fused with myeloma cells by standard somatic cell fusion procedures thus immortalizing these cells and yielding hybridoma cells. Such techniques are well known in the art (e. g. the hybridoma technique originally developed by Kohler and Milstein (1975) as well as other techniques such as the human B-cell hybridoma technique (Kozbor et al., 1983), the EBV-hybridoma technique to produce human monoclonal antibodies (Cole et al., *Methods Enzymol*, 121; 140-67 (1986)), and screening of combinatorial antibody libraries (Huse et al., *Science* 246; 1275 (1989)). Hybridoma cells can be screened immunochemically for production of antibodies specifically reactive with the target polypeptide(s) so that only monoclonal antibodies binding to said polypeptide(s) are isolated.

In particular, the antibody of the invention is a monoclonal antibody.

The antibody of the invention may be human, chimeric, humanized, murine, CDR-grafted, phage-displayed, bacteria-displayed, yeast-displayed, transgenic-mouse produced, mutagenized, and randomized.

A chimeric antibody is a molecule in which different portions are derived from different animal species, such as those having a variable region derived from a murine monoclonal antibody (mAb) and a human immunoglobulin constant region (See, e. g., Cabilly et al. (U.S. Pat. No. 4,816,567), and Boss et al. (U.S. Pat. No. 4,816,397)). Single-chain antibodies have an antigen binding site and consist of single polypeptides. They can be produced by techniques known in the art, for example using methods described in Ladner et al. (U.S. Pat. No. 4,946,778).

Humanized forms of antibodies of the invention are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin (recipient antibody) are replaced by corresponding non-human residues of the donor antibody. Furthermore, humanized antibodies may comprise residues that are not found in the recipient antibody or in the donor antibody. In general, the humanized antibody may comprise substantially all of at least one, and typically two, variable domains, in which all or substantially all of the hypervariable loops correspond to those of a non-human immunoglobulin (donor antibody having the desired specificity, affinity, and capacity) and all or substantially all of the FRs are those of a human immunoglobulin sequence. In one embodiment, humanized antibodies comprise a humanized FR that exhibits at least 65% sequence identity with an acceptor (non-human) FR, e.g., murine FR. The humanized antibody also may comprise at least a portion of an immunoglobulin constant region (Fc), particularly a human immunoglobulin. Methods for humanizing non-human antibodies have been described in the art. Preferably, a humanized antibody has one or more amino acid residues introduced into it from a source, which is non-human. These non-human amino acid residues are often referred to as "import" residues, which are typically taken from an "import" variable domain. Humanization may be essentially performed by substituting hypervariable region sequences for the corresponding sequences of a human antibody. Accordingly, such humanized antibodies are chimeric wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies. The choice of human variable domains, both light and heavy, to be used in making the humanized antibodies is very important to reduce antigenicity. Other methods generally involve conferring donor CDR binding affinity onto an antibody acceptor variable region framework. One method involves simultaneously grafting and optimizing the binding affinity of a variable region binding fragment. Another method relates to optimizing the binding affinity of an antibody variable region.

Multi-specific antibodies are antibody molecules having at least two antigen-binding sites that specifically bind different antigens. Such molecules can be produced by techniques known in the art, for example using methods described in Segal, U.S. Pat. No. 4,676,980 or U.S. Pat. No. 6,121,424. Monoclonal antibodies directed against the chemokines CXCL1, CXCL7 and CXCL8 can be identified and isolated by screening a recombinant combinatorial immunoglobulin library (e.g., an antibody phage display library) with the polypeptide(s) of interest. Kits for generating and screening phage display libraries are commercially available. Additionally, examples of methods and reagents particularly amenable for use in generating and screening antibody display library can be found in, for example, U.S. Pat. No. 5,223,409, WO 92/18619, and WO 91/17271.

Antibodies may be isolated after production (e.g., from the blood or serum of the animals) or synthetized and further purified by well-known techniques. Antibodies specific for a protein can be selected or purified by affinity chromatography, ELISPOT or ELISA. For example, the chemokines CXCL1, CXCL7 and CXCL8 can be covalently or non-covalently coupled to a solid support such as, for example, a chromatography column. The column can then be used to purify antibodies directed to the chemokines CXCL1, CXCL7 and CXCL8, from a sample containing antibodies directed against a large number of different epitopes, thereby generating a substantially purified antibody composition, i.e., one that is substantially free of contaminating antibodies. By a "substantially purified antibody composition" it is meant, in this context, that the antibody sample contains at most only 30% (by dry weight) of contaminating antibodies directed against epitopes other than those of the Strep-Tag II sequence, and preferably at most 20%, yet more preferably at most 10% and most preferably at most 5% (by dry weight) of the sample is contaminating antibodies. A "purified antibody composition" means that at least 99% of the antibodies in the composition are directed to the chemokines CXCL1, CXCL7 and CXCL8.

The antibodies of the invention may be administered in their "naked" or unconjugated form, or may have other agents conjugated to them. For examples the antibodies may be in detectably labeled form. Antibodies can be detectably labeled through the use of radioisotopes, affinity labels (such as biotin, avidin, etc.), enzymatic labels (such as horseradish peroxidase, alkaline phosphatase, etc.) fluorescent labels (such as FITC or rhodamine, etc.), paramagnetic atoms, and the like. Procedures for accomplishing such labeling are well known in the art.

In another embodiment, the antibody of the invention is lyophilized. In such embodiment, the lyophilized antibody is admixed with a carrier or diluent such as those hereinabove described at the time of administration. In yet another embodiment, the antibody of the invention is conjugated to a compound such as a polymer. In one embodiment, the polymer is a polyalkylene glycol. In one embodiment, the polyalkylene glycol is polyethylene glycol, or PEG.

For use in therapy, the antibody(ies) will be suitably formulated together with pharmaceutically acceptable excipients. Suitable formulations for the preventive or therapeutical treatment can be administered parenterally, preferably intra-arterially, intraperitoneally, intravenously, subcutaneously, intramuscularly or via an aerosol, and they will contain an effective amount of the antibody(ies). Said amount will vary depending on the general conditions of the patient, the progression of the disease and other factors.

In particular, the antibody of the invention is produced by the hybridoma deposited on 25, Apr. 2012 at the Collection Nationale de Cultures de Microorganismes (CNCM) under the number CNCM I-4617 (also designated by the inventors as 12A10-13).

In particular, the antibody of the invention is produced by the hybridoma deposited on 25, Apr. 2012 at the Collection Nationale de Cultures de Microorganismes (CNCM) under the number CNCM I-4618 (also designated by the inventors as 35B11-8).

The hybridomas CNCM I-4617 and CNCM I-4618 have been obtained by immunisation of LOU-M rat with a peptide specific for human CXCL7 but sharing similarities with human CXCL1 and 8, i.e. the peptide of sequence SDLY-AELRCMCIKTTSGIHPKNIQS (SEQ ID NO: 20). Different screening analysis were used to isolate these two hybridomas, i.e. ELISA tests on said peptide coupled to keyhole limpet hemocyanine and tests of the capacity of antibodies to inhibit CXCL-7 induced ERK activation in cells expressing CXCR2 as described in Bourcier et al. (2011).

These hybridomas produce high yields of antibodies of the invention.

The invention also relates to an isolated nucleic acid molecule encoding an antibody or a fragment thereof according to the invention.

The term "nucleic acid molecule" refers to a polymeric form of nucleotides, either deoxyribonucleotides or ribonucleotides, or analogs thereof.

The invention also relates to a vector comprising a nucleic acid molecule encoding an antibody or a fragment thereof according to the invention. Said vector can be appropriated for semi-stable or stable expression.

Particularly, said vector according to the invention is a cloning or an expression vector.

The vectors can be viral vectors such as bacteriophages or non-viral such as plasmids.

The invention also relates to a host cell comprising a nucleic acid molecule encoding an antibody or a fragment thereof according to the invention or a vector comprising said nucleic acid molecule.

The invention also relates to a pharmaceutical composition comprising at least one compound selected from the group consisting of:
  an antibody and a fragment thereof according to the invention,
  an isolated nucleic acid molecule encoding an antibody or a fragment thereof according to the invention; and
  a vector comprising said nucleic acid molecule. The advantageous embodiments are as defined above.

The terms "medicament" and "pharmaceutical compositions" are used interchangeably and in their broadest sense herein.

Such compound (in particular selected from the group consisting of an antibody and a fragment thereof according to the invention, an isolated nucleic acid molecule encoding an antibody according to the invention and a vector comprising said nucleic acid molecule) can be present in the pharmaceutical composition or medicament according to the invention in a therapeutically effective amount (active and non-toxic amount). A therapeutically effective amount refers to that amount of compound which ameliorates the symptoms or condition. Therapeutic efficacy and toxicity may be determined by standard pharmaceutical procedures in cell cultures or experimental animals, e.g., ED50 (the amount therapeutically effective in 50% of the population) and LD50 (the dose lethal to 50% of the population). The amount ratio of toxic to therapeutic effects is the therapeutic index and it can be expressed as the ratio, LD50/ED50. Pharmaceutical compositions which exhibit large therapeutic indices are preferred.

For example, the antibody according to the invention, can be administered to a patient, in particular intravenously, in an amount, within the range from 0.1 µg/kg to 100 mg/kg, particularly from 1 mg/kg to 50 mg/kg of body weight of said patient at least every month, particularly at least every three weeks, more particularly at least every two weeks and even more particularly at least every week.

The pharmaceutical composition according to the invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingualrectal means or ocular.

In addition to the active ingredients, the pharmaceutical composition of the invention may contain suitable pharmaceutically acceptable carriers comprising excipients and auxiliaries, which facilitate processing of the active compounds into preparations which can be used pharmaceutically. In particular, the pharmaceutical composition according to the invention is formulated in a pharmaceutical acceptable carrier. Pharmaceutical acceptable carriers are well known by one skilled in the art. Further details on techniques for formulation and administration may be found in the latest edition of Remington's Pharmaceutical Sciences (Maack Publishing Co., Easton, Pa.).

In particular, the pharmaceutical acceptable carrier comprises or is an isotonic solution.

The invention also relates to an antibody or a fragment thereof according to the invention for use as a medicament. The advantageous embodiments are as defined above.

The invention also relates to an isolated nucleic acid molecule encoding an antibody or a fragment thereof according to the invention for use as a medicament. The advantageous embodiments are as defined above.

The invention also relates to a vector comprising a nucleic acid molecule encoding an antibody according to the invention for use as a medicament. The advantageous embodiments are as defined above.

The invention also relates to an antibody or a fragment thereof according to the invention for use in the treatment and/or prevention of diseases related to the chemokines CXCL1, CXCL7 and CXCL8, particularly of pathological angiogenesis diseases. The advantageous embodiments are as defined above.

The invention also relates to an isolated nucleic acid molecule encoding an antibody or a fragment thereof according to the invention for use in the treatment and/or prevention of diseases related to the chemokines CXCL1, CXCL7 and CXCL8, particularly of pathological angiogenesis diseases. The advantageous embodiments are as defined above.

The invention also relates to a vector comprising an isolated nucleic acid molecule encoding an antibody or a fragment thereof according to the invention for use in the treatment and/or prevention of diseases related to the chemokines CXCL1, CXCL7 and CXCL8, particularly of pathological angiogenesis diseases. The advantageous embodiments are as defined above.

As used herein, the term "disease related to the chemokines CXCL1, CXCL7 and CXCL8" refers to any disease wherein at least one, particularly at least two and more particularly wherein all said chemokines are involved. Diseases related to the chemokines CXCL1, CXCL7 and CXCL8 include pathological angiogenesis diseases and inflammatory diseases. For example, inflammatory diseases related to the chemokines CXCL1, CXCL7 and CXCL8 can be ophthalmological diseases, like glaucoma, wet age-related macular degeneration, diabetic retinopathies. Inflammatory diseases also include asthma and rheumatoid arthritis (which is also an angiogenesis disease).

As used herein, the term "pathological angiogenesis disease" refers to any disease, wherein the abnormal proliferation of endothelial cells leads to a pathological development of a vascular network. Examples of pathological angiogenesis diseases are described in the article of Carmeliet et al., 2000. Angiogenesis may be a therapeutic target for combating diseases characterized by abnormal vasculature, therefore the expressions "pathological angiogenesis disease", "pathological angiogenesis disorder", "disease characterized by undesirable excessive neovascularization", "disorder characterized by undesirable excessive neovascularization", "disease involving an undesirable pathological angiogenesis", "disorder involving an undesirable pathological angiogenesis", "disease whereas there is a need to inhibit angiogenesis" or "disorder whereas there is a need to inhibit angiogenesis" may be used interchangeably.

In particular, pathological angiogenesis diseases, or diseases characterized by undesirable excessive neovascularization, are selected from the group consisting of:

cancers with abnormal angiogenesis, in particular solid tumors with abnormal angiogenesis, more particularly renal cancers including clear cell renal cell carcinoma, breast cancers, ovarian cancers, lung cancers, pancreatic cancers and colon cancers;

ophthalmological diseases with abnormal angiogenesis, in particular age-related macular degeneration, diabetic retinopathy, retinitis pigmentosa and uveitis;

rheumatoid arthritis;

psoriasis;

angioma;

endometriosis;

and kaposi sarcoma.

Particularly, said pathological angiogenesis disease is a clear cell renal cell carcinoma.

The invention also relates to the use of at least one compound selected from the group consisting of:
an antibody and a fragment thereof according to the invention,
an isolated nucleic acid molecule encoding an antibody or a fragment thereof according to the invention; and
a vector comprising said nucleic acid molecule;
for the preparation of a medicament for the treatment and/or prevention of diseases related to the chemokines CXCL1, CXCL7 and CXCL8, particularly of pathological angiogenesis diseases, or diseases characterized by undesirable excessive neovascularization.

The invention also relates to a method of treatment and/or prophylaxis of diseases related to the chemokines CXCL1, CXCL7 and CXCL8, particularly of pathological angiogenesis diseases, or diseases characterized by undesirable excessive neovascularization, said method comprises the step of administering to a patient in need thereof a therapeutically or prophylactic amount of at least one compound selected from the group consisting of:
an antibody and a fragment thereof according to the invention,
an isolated nucleic acid molecule encoding an antibody or a fragment thereof according to the invention; and
a vector comprising said nucleic acid molecule.

The therapeutic method according to the invention can further comprise the step of administering to a patient in need thereof of a therapeutically or prophylactic amount of at least another compound of interest (e.g. an anti-tumor agent, an anti-angiogenic compound, an anti-inflammatory compound).

As used herein, the term "anti-tumor agent" refers to any compound that prevents tumor growth or promotes tumor shrinking Anti-tumor agents can be anti-angiogenic compounds, DNA Intercalators/Cross-linkers (like oxaliplatin, mitoxantrone), DNA Synthesis Inhibitors (like cytosine β-D-arabinofuranoside, 5-Fluorouracil), DNA-RNA Transcription Regulators (doxorubicin, actinomycin D), Microtubule Inhibitors (paclitaxel, nocodazole).

As used herein, the term "anti-angiogenic compound" refers to any compound that inhibits the development of a pathological vascular network. In particular, the anti-angiogenic compound can inhibit receptors of pro-angiogenic factors like VEGF receptors and receptors of CXCL/ELR+ chemokines (e.g. CXCR1 and CXCR2).

As used herein, the term "anti-inflammatory compound" refers to any compound that reduces inflammation. In particular, anti-inflammatory compound can be corticoid and non-steroid anti-inflammatory agent ibuprofen derivative.

In particular, the anti-angiogenic compounds are selected from the group consisting of:

Antibodies anti-VEGF, like bevacizumab (particularly for the treatment and/or prevention of cancers) and ranibizumab (particularly for the treatment and/or prevention of age-related macular degeneration);

Antibodies anti-EGF receptor, like cetuximab;

Inhibitors of receptors involve in angiogenesis including VEGFR1, 2, 3, CSFR, PDGFR, like sunitinib, sorafenib, axitinib, regorafenib;

Inhibitors of m-TOR, like everolimus, temsirolimus;

Inhibitors of EGF receptor, like erlotinib.

Said antibody, nucleic acid molecule and/or said vector according to the invention can be administrated simultaneously, separately or sequentially of said compound of interest.

The invention also relates to a combination product, which comprises:
at least one compound selected from the group consisting of an antibody and a fragment thereof according to the invention, an isolated nucleic acid molecule encoding an antibody or a fragment thereof according to the invention and a vector comprising said nucleic acid molecule; and
at least another compound of interest;
for simultaneous, separate or sequential use as a medicament.

The advantageous embodiments are as defined above.

In particular, said another compound of interest is an anti-angiogenic compound.

The invention also relates to the combination product according to the invention, for its use for the prevention and/or treatment of diseases related to the chemokines CXCL1, CXCL7 and CXCL8, particularly of pathological angiogenesis diseases.

The invention also relates to a method for detecting in a sample at least one chemokine selected from the group consisting of CXCL 1, CXCL7 and CXCL8, comprising the step of incubating said sample with the antibody and/or fragment thereof according to the invention.

In particular, said sample is a biological sample.

The term "biological sample" encompasses a variety of sample types obtained from an organism that may be used in a diagnostic or monitoring assay. The term encompasses blood and other liquid samples of biological origin, solid tissue samples, such as a biopsy specimen, or tissue cultures or cells derived there from and the progeny thereof. Additionally, the term may encompass circulating tumor or other cells. The term specifically encompasses a clinical sample, and further includes cells in cell culture, cell supernatants, cell lysates, serum, plasma, urine, amniotic fluid, biological fluids including aqueous humour and vitreous for eyes samples, and tissue samples. The term also encompasses samples that have been manipulated in any way after procurement, such as treatment with reagents, solubilisation, or enrichment for certain components.

Advantageously, the biological sample can be selected from the group comprising a bodily fluid, a fraction thereof, tissue extract and, cell extract. Particularly the biological sample can be selected from the group comprising plasma sample and tumor extract.

In particular, the method for detecting in a sample a chemokine according to the invention further comprises the step of detecting the binding of the antibody according to the invention with at least one chemokine selected from the group consisting of CXCL 1, CXCL7 and CXCL8.

The method for detecting in a sample a chemokine according to the invention can be based on various techniques, well known by one skilled in the art, including, but not limited to:

- a western blot assay (the chemokine or fragment thereof present in a cell lysate or in a solution being immobilized on a membrane, the said membrane being thereafter incubated with the antibody of the invention, preferably labeled, in appropriate conditions well-known in the art),
- an ELISA assay (the chemokine or fragment thereof being immobilized on a microtiter plate, the said plate being thereafter incubated with the antibody of the invention, preferably labeled, in appropriate conditions well-known in the art),
- an immunohistochemistry assay (the recombinant antibody, preferably labeled, being used to stain a sample containing fixed cells or tissues expressing the chemokine or fragment thereof),
- a flow cytometry assay (the recombinant antibody, preferably labeled, being used to stain a sample containing fixed or living cells expressing the chemokine or fragment thereof, in appropriate conditions well-known in the art), In one embodiment of the method for detecting in a sample a chemokine according to the invention, the antibody of the invention is coated on a solid support.

These detection techniques are well-described in Sambrook, Fritsch and Maniatis—"Molecular Cloning—A Laboratory Manual" Second Edition *Cold Spring Harbor Laboratory,* 1989. Any other detection techniques requiring the use of an antibody are herein encompassed. The presence and eventually the amount of said chemokine(s) in said sample can be determined thanks to these techniques. Some of these techniques require labeling the antibody of the invention with a detectable marker, preferably a fluorescent or a luminescent marker, as disclosed above.

The invention also relates to a method for purifying from a sample a chemokine selected from the group consisting of the chemokines CXCL1, CXCL7 and CXCL8, comprising the step of incubating said sample with the antibody and/or fragment thereof according to the invention.

The method for purifying from a sample a chemokine according to the invention can be based on various techniques, well known by one skilled in the art, including, but not limited to flow cytometry assays, immunoprecipitation assays. These detection techniques are well-described in Sambrook, Fritsch and Maniatis—"Molecular Cloning—A Laboratory Manual" Second Edition Cold Spring Harbor Laboratory, 1989.

The invention also relates to a kit useful for carrying the methods for detecting in a sample a chemokine and for purifying from a sample a chemokine according to the invention; said kit comprising:

- at least one antibody and/or fragment thereof according to the invention; and
- at least one reagent for detecting said antibody and/or fragment thereof according to the invention.

Said reagent for detecting said antibody according to the invention can be selected from the group consisting of ELISA reagents, Western blot reagents, and dot blot reagents.

The invention also relates to in vitro or ex vitro diagnostic and/or prognostic method, and particularly to an in vitro diagnostic and/or prognostic method of a disease related to the chemokines CXCL1, CXCL7 and CXCL8, particularly of a pathological angiogenesis disease, in particular of clear cell renal cell carcinoma, in a subject, said method comprising:

determining the expression and/or the level of expression of at least one human chemokine chosen in the group consisting of CXCL1, CXCL7 and CXCL8 in a biological sample of said subject using at least one antibody and/or fragment thereof according to the invention. In fact, the inventors have demonstrated that the chemokines CXCL1, CXCL7 and CXCL8 are prognostic factors for overall survival of patients affected with a disease related to the chemokines CXCL1, CXCL7 and CXCL8, a pathological angiogenesis disease, clear cell renal cell carcinoma. In particular, the inventors have shown that the overexpression of these chemokines, in particular of CXCL1 and CXCL7, is a factor of poor prognosis for overall survival.

In particular, step i) can be performed by further using at least one labelled secondary antibody directed to one chemokine CXCL1, CXCL7 and CXCL8, wherein said chemokine recognizes the antibody and/or fragment thereof of the invention.

For example, step i) can be performed by an ELISA assay, wherein the antibody or fragment thereof of the invention is immobilized on a microtiter plate, said plate being thereafter incubated with at least one labelled secondary antibody directed to one chemokine CXCL1, CXCL7 and CXCL8, which recognize the antibody and/or fragment thereof according to the invention, in appropriate conditions well-known in the art. According to this embodiment, the expression level of the three chemokines can be determined simultaneously.

The method of the invention can further comprises the step ii) of comparing said level of expression determined at step i) to a control level and determining if said subject is affected with a disease related to the chemokines CXCL1, CXCL7 and CXCL8, particularly with a pathological angiogenesis disease, more particularly with a clear cell renal cell carcinoma.

In a preferred embodiment, the method of the invention comprises the step ii) of comparing said level of expression determined at step i) to a control level and determining if said level of expression determined at step i) is significantly higher than said control level; said significantly higher level of expression indicates that the subject is affected with a disease related to the chemokines CXCL1, CXCL7 and CXCL8, particularly with a pathological angiogenesis disease, more particularly with clear cell renal cell carcinoma; wherein said control level is the expression level of said at least one chemokine determined in at least a biological sample from an healthy subject, or from a subject who is not affected with a disease related to the chemokines CXCL1, CXCL7 and CXCL8, particularly with a pathological angiogenesis disease, more particularly with clear cell renal cell carcinoma.

The invention also relates to in vitro or ex vitro method to determine a pejorative outcome of a disease related to the chemokines CXCL1, CXCL7 and CXCL8, particularly of a pathological angiogenesis disease, more particularly of clear cell renal cell carcinoma, in a subject, said method comprising:

a) determining the expression and/or the level of expression of at least one human chemokine chosen in the group consisting of CXCL1, CXCL7 and CXCL8 in a biological sample of said subject using at least one antibody and/or fragment thereof according to the invention.

The method of the invention can further comprises the step b) of comparing said level of expression determined at step a) to a control level and determining if said subject is or not undergoing a pejorative outcome of a disease related to the chemokines CXCL1, CXCL7 and CXCL8, particularly of a pathological angiogenesis disease, more particularly of a clear cell renal cell carcinoma.

In particular, step a) can be performed by further using at least one labelled secondary antibody directed to one chemokine CXCL1, CXCL7 and CXCL8, which recognize the antibody and/or fragment thereof of the invention.

For example, step a) can be performed by an ELISA assay, wherein the antibody or fragment thereof of the invention is immobilized on a microtiter plate, said plate being thereafter incubated with at least one labelled secondary antibody directed to one chemokine CXCL1, CXCL7 and CXCL8, which recognize the antibody and/or fragment thereof according to the invention, in appropriate conditions well-known in the art. According to this embodiment, the expression level of the three chemokines can be determined simultaneously.

Suitable "control level" include the expression level of said at least one chemokine determined in at least one reference sample and a reference threshold value.

A "reference sample" is a biological sample from a subject with a known state of disease related to the chemokines CXCL1, CXCL7 and CXCL8, particularly a known pathological angiogenesis disease state, more particularly a known clear cell clear cell renal cell carcinoma state, or from a healthy subject, or from a subject who is not affected with a disease related to the chemokines CXCL1, CXCL7 and CXCL8, particularly with a pathological angiogenesis disease, more particularly with clear cell renal cell carcinoma.

Preferably, the control level is the mean expression levels of said at least one chemokine determined in several reference samples, from several subjects.

Preferably, the reference sample is the same type of biological sample (i. e. a biological sample of corresponding physiological nature) than said biological sample of step i) or a).

In a preferred embodiment, the method of the invention comprises the step b) of comparing said level of expression determined at step a) to a control level and determining if said level of expression determined at step a) is significantly higher than said control level; said significantly higher level of expression indicates a pejorative outcome of disease related to the chemokines CXCL1, CXCL7 and CXCL8, particularly of pathological angiogenesis disease, more particularly of clear cell renal cell carcinoma in said subject; wherein said control level is the expression level of said at least one chemokine determined in at least a biological sample from a healthy subject, or from an subject who is not affected with a disease related to the chemokines CXCL1, CXCL7 and CXCL8, particularly with a pathological angiogenesis disease, more particularly with clear cell renal cell carcinoma.

Suitable "control level" include the expression level of said at least one chemokine determined in the same type of biological sample of a healthy subject, of an subject who is not affected with a disease related to the chemokines CXCL1, CXCL7 and CXCL8, particularly with a pathological angiogenesis disease, more particularly with clear cell renal cell carcinoma.

Preferably, the control level is the mean expression levels of said at least one chemokine determined in the same type of biological sample of several healthy subjects, of several subjects who are not affected with a disease related to the chemokines CXCL1, CXCL7 and CXCL8, particularly with a pathological angiogenesis disease, more particularly with clear cell renal cell carcinoma Said significant higher level of expression of said at least one chemokine can corresponds to an increase of expression of at least more than 10%, more than 15%, more than 20%, more than 25%, more than 30%, preferably more than 35% of said control level.

Such a reference threshold value may vary depending on the type of tested biological sample and the method used for determining the level of expression of said at least one chemokine. However, for particular experimental conditions (same type of tested biological sample, same method for determining the level of expression of said at least one chemokine), said threshold value may be determined based on a reference pool of patients comprising both a population of patients with stable disease related to the chemokines CXCL1, CXCL7 and CXCL8, particularly stable pathological angiogenesis disease, more particularly stable clear cell renal cell carcinoma (alive patients) and a population of patients undergoing a pejorative outcome of disease related to the chemokines CXCL1, CXCL7 and CXCL8, particularly of pathological angiogenesis disease, in particular clear cell renal cell carcinoma (deceased patients). By measuring the levels of expression of said at least one chemokine of these patients, a reference threshold value T can be determined by the following features:

- all or most reference patients with stable disease related to the chemokines CXCL1, CXCL7 and CXCL8, particularly stable pathological angiogenesis disease, more particularly stable clear cell renal cell carcinoma (alive patients) have at least one chemokine expression level values inferior to T; and
- all or most reference patients undergoing a pejorative outcome of disease related to the chemokines CXCL1, CXCL7 and CXCL8, particularly of pathological angiogenesis disease, more particularly of clear cell renal cell carcinoma (deceased patients) have at least one chemokine expression level values superior to T.

In this case, if said level of expression determined at step i) is significantly higher than said threshold value T, it indicates a pejorative outcome of disease related to the chemokines CXCL1, CXCL7 and CXCL8, particularly of pathological angiogenesis disease, more particularly of clear cell renal cell carcinoma in said subject.

Particularly, if the tested biological sample is a plasma sample, the reference threshold value can be comprised:
- in the range of 265 to 1825 ng/ml, preferably 450 to 800 ng/ml and more preferably 640 ng/ml for CXCL7;
- in the range of 0 to 30 pg/ml, preferably 5 to 15 pg/ml and more preferably 11 pg/ml for CXCL8.

Particularly, if the tested biological sample is a tumor lysate sample, the reference threshold value can be comprised:
- in the range of 50 to 150 pg/mg, preferably 75 to 125 pg/mg and more preferably 96 pg/mg of total proteins for CXCL1;
- in the range of 800 to 1400 pg/mg, preferably 1000 to 1200 pg/mg and more preferably 1152 pg/mg of total proteins for CXCL7;
- in the range of 50 to 350 pg/mg, preferably 150 to 250 pg/mg and more preferably 206 pg/mg of total proteins for CXCL8.

In one embodiment of the method of the invention to determine a pejorative outcome of pathological angiogenesis disease, in particular clear cell renal cell carcinoma in a subject, said subject is subjected to an antiangiogenic therapy.

The antiangiogenic therapy can comprise the administration to said subject of an anti-angiogenic compound.

The term "determination" as used herein may mean both qualitatively detecting and quantifying.

The term "expression" generally refers to the process by which a polynucleotide sequence undergoes successful transcription and translation such that detectable levels of the amino acid sequence or protein are expressed. In certain contexts herein, expression refers to the production of mRNA. In other contexts, expression refers to the production of protein or fragments thereof. The fragments may be produced via enzymatic cleavage or biological processes characteristic of normal or diseased conditions.

Any of a variety of known methods may be used for detection of said at least one chemokine in said biological sample of said individual, including, but not limited to, immunoassay, using antibody or fragment thereof according to the invention, e.g., by enzyme-linked immunosorbent assay (ELISA), radioimmunoassay (RIA), and the like.

The invention also relates to a kit for carrying out the in vitro or ex vitro diagnostic and/or prognostic method of a disease related to the chemokines CXCL1, CXCL7 and CXCL8, particularly of a pathological angiogenesis disease in a subject of the invention, said kit comprises at least one antibody and/or fragment thereof according to the invention.

In a particular embodiment, the invention also relates to a kit for carrying out the in vitro diagnostic and/or prognostic method of a disease related to the chemokines CXCL1, CXCL7 and CXCL8, particularly of a pathological angiogenesis disease or a disease or disorder characterized by undesirable excessive neovascularization in a subject, said kit comprises at least one antibody and/or fragment thereof according to the invention.

The kit may provide additional components that are useful in methods of the invention, including, but not limited to, buffers, developing reagents, labels, reacting surfaces, means for detection, control samples, standards, instructions, and interpretive information for determining if a subject is affected with a disease related to the chemokines CXCL1, CXCL7 and CXCL8, particularly with a pathological angiogenesis disease, more particularly with a clear cell renal cell carcinoma.

The kit can also comprise:
at least one reagent for detecting said antibody or fragment thereof according to the invention.

The invention also relates to a kit for carrying out the method of the invention to determine a pejorative outcome of disease related to the chemokines CXCL1, CXCL7 and CXCL8, particularly of pathological angiogenesis disease, more particularly of clear cell renal cell carcinoma in a subject according to the invention, said kit comprises at least one antibody and/or fragment thereof according to the invention.

The kit may provide additional components that are useful in methods of the invention, including, but not limited to, buffers, developing reagents, labels, reacting surfaces, means for detection, control samples, standards, instructions, and interpretive information for determining the pejorative outcome of disease related to the chemokines CXCL1, CXCL7 and CXCL8, particularly of a pathological angiogenesis disease, more particularly of clear cell renal cell carcinoma in a subject.

The kit can also comprise:
at least one reagent for detecting said antibody or fragment thereof according to the invention.

The invention also relates to a method comprising:
i") diagnosing and/or prognosticating a disease related to the chemokines CXCL1, CXCL7 and CXCL8, particularly a pathological angiogenesis disease, more particularly clear cell renal cell carcinoma, in a subject, in particular according to the method of the invention; and
iii") treating a subject affected with a disease related to the chemokines CXCL1, CXCL7 and CXCL8, particularly a pathological angiogenesis disease, more particularly with clear cell renal cell carcinoma, with an anti-inflammatory and/or antiangiogenic therapy, particularly administrating an anti-inflammatory compound and/or an antiangiogenic compound (in particular at least one compound selected from the group consisting of antibody, fragment thereof, nucleic acid molecule, vector according to the invention) to said subject affected with a disease related to the chemokines CXCL1, CXCL7 and CXCL8, particularly a pathological angiogenesis disease.

In particular, said method comprises:
i") diagnosing and/or prognosticating a disease related to the chemokines CXCL1, CXCL7 and CXCL8, particularly a pathological angiogenesis disease, more particularly clear cell renal cell carcinoma, in a subject, comprising the determination of the expression and/or the level of expression of at least one human chemokine chosen in the group consisting of CXCL1, CXCL7 and CXCL8 in a biological sample of said subject; and
iii") treating a subject affected with a disease related to the chemokines CXCL1, CXCL7 and CXCL8, particularly a pathological angiogenesis disease, more particularly with clear cell renal cell carcinoma, with an anti-inflammatory and an antiangiogenic therapy, comprising the administration of at least one compound selected from the group consisting of antibody, fragment thereof, nucleic acid molecule, vector according to the invention to said subject affected with a disease related to the chemokines CXCL1, CXCL7 and CXCL8, particularly a pathological angiogenesis disease. Such a method has the advantage of better tailor the treatment of patients (with overexpression of chemokines CXCL1, CXCL7 and/or CXCL8) and thus avoids unnecessary treatment of patients with anti-VEGF therapies (thus avoid relapse and disease progression to death). In a preferred embodiment, said method of the invention further comprises the step of ii") comparing said level of expression determined at step i") to a control level and determining if said level of expression determined at step i") is significantly higher than said control level; said significantly higher level of expression indicates a pejorative outcome of disease related to the chemokines CXCL1, CXCL7 and CXCL8, particularly of pathological angiogenesis disease, more particularly of clear cell renal cell carcinoma in said subject; wherein said control level is the expression level of said at least one chemokine determined in at least a biological sample from a healthy subject, or from an subject who is not affected with a disease related to the chemokines CXCL1, CXCL7 and CXCL8, particularly with a pathological angiogenesis disease, more particularly with clear cell renal cell carcinoma.

The invention also relates to a method comprising:
i"") determining a pejorative outcome of a disease related to the chemokines CXCL1, CXCL7 and CXCL8, particularly of pathological angiogenesis disease, more particularly of clear cell renal cell carcinoma in a subject, in particular according to the method of the invention;

iii"") treating a subject who is undergoing a pejorative outcome of a disease related to the chemokines CXCL1, CXCL7 and CXCL8, particularly of a pathological angiogenesis disease, more particularly of clear cell renal cell carcinoma with an anti-inflammatory therapy and/or antiangiogenic therapy, particularly administrating anti-inflammatory compound and/or an antiangiogenic compound (in particular at least one compound selected from the group consisting of antibody, fragment thereof, nucleic acid molecule, vector according to the invention) to said subject who is undergoing a pejorative outcome of a disease related to the chemokines CXCL1, CXCL7 and CXCL8, particularly of a pathological angiogenesis disease.

In particular, said method comprises:

i"") determining a pejorative outcome of a disease related to the chemokines CXCL1, CXCL7 and CXCL8, particularly of pathological angiogenesis diseasemore particularly of clear cell renal cell carcinoma, in a subject, comprising the determination of the expression and/or the level of expression of at least one human chemokine chosen in the group consisting of CXCL1, CXCL7 and CXCL8 in a biological sample of said subject; and iii"") treating a subject who is undergoing a pejorative outcome of a disease related to the chemokines CXCL1, CXCL7 and CXCL8, particularly of a pathological angiogenesis disease, more particularly of clear cell renal cell carcinoma, with an anti-inflammatory and an antiangiogenic therapy, comprising the administration of at least one compound selected from the group consisting of antibody, fragment thereof, nucleic acid molecule, vector according to the invention to said subject who is undergoing a pejorative outcome of a disease related to the chemokines CXCL1, CXCL7 and CXCL8, particularly of a pathological angiogenesis disease. Such a method has the advantage of better tailor the treatment of patients (with overexpression of chemokines CXCL1, CXCL7 and/or CXCL8) and thus avoids unnecessary treatment of patients with anti-VEGF therapies (thus avoid relapse and disease progression to death). In a preferred embodiment, said method of the invention further comprises the step of ii"") comparing said level of expression determined at step i"") to a control level and determining if said level of expression determined at step i"") is significantly higher than said control level; said significantly higher level of expression indicates a pejorative outcome of disease related to the chemokines CXCL1, CXCL7 and CXCL8, particularly of pathological angiogenesis disease, more particularly of clear cell renal cell carcinoma in said subject; wherein said control level is the expression level of said at least one chemokine determined in at least a biological sample from a healthy subject, or from an subject who is not affected with a disease related to the chemokines CXCL1, CXCL7 and CXCL8, particularly with a pathological angiogenesis disease, more particularly with clear cell renal cell carcinoma.

The invention also relates to a peptide selected from the group consisting of:

a peptide of sequence comprising or consisting of the sequence SEQ ID NO: 20 and a peptide of sequence comprising or consisting of a sequence having at least 80%, at least 85%, at least 90%, at least 95% of identity with SEQ ID NO: 20 over the entire length of SEQ ID NO: 20.

The invention also relates to the use of at least one peptide of the invention selected from the group consisting of:

a peptide of sequence comprising or consisting of the sequence SEQ ID NO: 20 and a peptide of sequence comprising or consisting of a sequence having at least 80%, at least 85%, at least 90%, at least 95% of identity with SEQ ID NO: 20 over the entire length of SEQ ID NO: 20;

as an immunogenic peptide.

As used herein, the term "immunogenic peptide" relates to a peptide useful to immunise an animal that is recognized by T cells primed immunization.

The peptide immunogenicity can be increased by cross-linking or coupling with immunogenic carriers, or by use of suitable adjuvants. The determination of suitable immunogenic carriers, or suitable adjuvants is well within the capability of those skilled in the art. Examples of immunogenic carriers include but are not limited to keyhole limpet hemocyanin (KHL), tetanus toxoid (TT), bovine serum albumin (BSA), ovalbumin (OVA), bovine thyroglobulin (BTG), Gluthation S Transferase (GST), bovine thyroglobulin or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCL_2$, or $R^1N=C=NR$, where $R^1$ and R are different alkyl groups, particularly keyhole limpet hemocyanin (KLH).

The invention also relates to an immunogenic composition comprising at least one peptide of the invention selected from the group consisting of:

a peptide of sequence comprising or consisting of the sequence SEQ ID NO: 20 and a peptide of sequence comprising or consisting of a sequence having at least 80%, at least 85%, at least 90%, at least 95% of identity with SEQ ID NO: 20 over the entire length of SEQ ID NO: 20.

The invention also relates to a peptide of the invention selected from the group consisting of:

a peptide of sequence comprising or consisting of the sequence SEQ ID NO: 20 and a peptide of sequence comprising or consisting of a sequence having at least 80%, at least 85%, at least 90%, at least 95% of identity with SEQ ID NO: 20 over the entire length of SEQ ID NO: 20, for use as a medicament, in particular for the prevention and/or treatment of diseases related to the chemokines CXCL1, CXCL7 and CXCL8, particularly of pathological angiogenesis diseases, more particularly of clear cell renal cell carcinoma.

For use in prevention or therapy, the peptide will be suitably formulated together with pharmaceutically acceptable excipients. Suitable formulations for the preventive or therapeutical treatment can be administered orally or parenterally, preferably subcutaneously or intramuscularly, and they will contain an effective amount of the peptide. Said amount should be able to elicit a humoral or cell-mediated immune response directed against at least one chemokine chosen in the group comprising CXCL1, CXCL7 and CXCL8 and will vary depending on the general conditions of the patient, the progression of the disease and other factors.

In another embodiment, the peptide of the invention is lyophilized. In such embodiment, the lyophilized peptide of the invention is admixed with a carrier or diluent such as those hereinabove described at the time of administration. In yet another embodiment, the antibody of the invention is conjugated to a compound such as a polymer. In one embodiment, the polymer is a polyalkylene glycol. In one embodiment, the polyalkylene glycol is polyethylene glycol, or PEG.

The invention also relates to a pharmaceutical composition comprising a peptide of the invention selected from the group consisting of:
  a peptide of sequence comprising or consisting of the sequence SEQ ID NO: 20 and a peptide of sequence comprising or consisting of a sequence having at least 80%, at least 85%, at least 90%, at least 95% of identity with SEQ ID NO: 20 over the entire length of SEQ ID NO: 20.

The invention also relates to a peptide of the invention selected from the group consisting of:
  a peptide of sequence comprising or consisting of the sequence SEQ ID NO: 20 and a peptide of sequence comprising or consisting of a sequence having at least 80%, at least 85%, at least 90%, at least 95% of identity with SEQ ID NO: 20 over the entire length of SEQ ID NO: 20,
    for the preparation of a medicament for the prevention and/or treatment of diseases related to the chemokines CXCL1, CXCL7 and CXCL8, particularly of pathological angiogenesis diseases, more particularly of clear cell renal cell carcinoma.

The invention also relates to a method of treatment and/or prophylaxis of diseases related to the chemokines CXCL1, CXCL7 and CXCL8, particularly of pathological angiogenesis diseases, said method comprises the step of administering to a patient in need thereof a therapeutically or prophylactic amount of at least one peptide of the invention selected from the group consisting of:
  a peptide of sequence comprising or consisting of the sequence SEQ ID NO: 20 and a peptide of sequence comprising or consisting of a sequence having at least 80%, at least 85%, at least 90%, at least 95% of identity with SEQ ID NO: 20 over the entire length of SEQ ID NO: 20.

The invention also relates to a method for preparing an antibody directed to the chemokines CXCL1, CXCL7 and CXCL8, comprising the steps of:
  α) immunising a non-human animal by repeated administration of at least one peptide chosen in the group consisting of:
    a peptide of sequence comprising or consisting of the sequence SEQ ID NO: 20 and a peptide of sequence comprising or consisting of a sequence having at least 80%, at least 85%, at least 90%, at least 95% of identity with SEQ ID NO: 20 over the entire length of SEQ ID NO: 20;
    and/or of at least one expression vector comprising a nucleotide sequence encoding said at least one peptide under the control of a promoter, which is effective in cells of said non-human animal; and
  β) collecting the resulting serum from said immunised non-human animal to obtain antibodies directed against said at least one peptide;
  χ) determining in vitro or ex vivo the ability of said antibodies obtained at said step β) to specifically bind to the chemokines CXCL1, CXCL7 and CXCL8; and eventually
  δ) selecting antibody(ies), which is (are) able to specifically bind said chemokines CXCL1, CXCL7 and CXCL8.

Preferably, the method for preparing an antibody directed to the chemokines CXCL1, CXCL7 and CXCL8, further comprises fixing said serum antibodies to a backing substrate, preferably a solid support, most preferably a polystyrene solid support.

Suitable non-human animals include but are not limited to mouse, rat, sheep, goat, hamster, rabbit, preferably mouse.

The peptide used as immunogenic peptide in step a) may comprise the complete peptide, or fragments and derivatives thereof, which are able to elicit a humoral immune response directed against the chemokines CXCL1, CXCL7 and CXCL8.

The serum of said animal can be sampled for evaluation of antibody titer. When the optimal titer has been reached, the animal can be bled to yield a suitable volume of specific serum. The degree of antibody purification required depends on the intended application. For certain purposes, there is no requirement at all for purification, however, in other cases, such as where the antibody is to be immobilised on a solid support, purification steps can be taken to remove undesired material and reduce or eliminate nonspecific binding.

Step χ) of determining in vitro or ex vivo the ability of said antibodies obtained at said step β) to specifically bind the chemokines CXCL1, CXCL7 and CXCL8, can be readily determined by one skilled in the art, for example, by Scatchard analysis (1949) or surface Plasmon resonance analysis as described hereafter.

The term "a nucleotide sequence encoding said at least one peptide under the control of a promoter, which is effective in cells of said non-human animal" relates to a nucleotide sequence coding said encoding said at least one peptide, which is operatively linked to a promoter, which directs the expression of said nucleotide sequence in cells of said non-human animal.

In general, the vectors useful in the invention include but are not limited to plasmids, phagemids, viruses, other vehicles derived from viral or bacterial sources, which have been manipulated by the insertion or incorporation of a nucleotide sequence encoding said at least one peptide.

The expression of said at least one peptide can be stable or transitory expression, using stable or transitory expression vectors, respectively. Example of transitory expression vectors include, plasmids. Examples of stable expression vectors include lentiviruses vectors. Preferably, the expression of said at least one peptide is stable.

The expression of said at least one peptide can also be constitutive or inducible, using constitutive or inducible promoters, which are well known by one skilled in the art. Examples of constitutive promoters include mammalian or viral promoters like beta-actin promoter, muscle creatine kinase promoter, human elongation factor, promoters from the simian virus (e.g., SV40), papilloma virus, adenovirus, human immunodeficiency virus (HIV), cytomegalovirus (CMV), Rous sarcoma virus (RSV), hepatitis B virus (HBV), the long terminal repeats (LTR) of Moloney leukemia virus and other retroviruses, and the thymidine kinase promoter of herpes simplex virus. One can readily use other constitutive promoters not named but known in the art.

The promoters useful for the invention also include inducible promoters, which are expressed in the presence of an inducing agent. For example, the metallothionein promoter is induced to promote transcription and translation in the presence of certain metal ions.

Preferably, the expression of said at least one peptide is constitutive.

In particular step δ) can comprise the selection of antibody(ies), which is (are) capable of binding to the human chemokine CXCL1 with an equilibrium dissociation constant ($K_D$) of at most 16 nM, to the human chemokine CXCL7 with an equilibrium dissociation constant ($K_D$) of at most 5 nM and to the human chemokine CXCL8 with an equilibrium dissociation constant ($K_D$) of at most 45 nM, as determined by surface plasmon resonance.

The invention also relates to a method for selecting antibodies for the treatment of diseases related to the chemokines CXCL1, CXCL7 and CXCL8, particularly of pathological angiogenesis diseases, comprising the step of:

a") immunising a non-human animal by repeated administration of at least one peptide chosen in the group comprising:

a peptide of sequence comprising or consisting of the sequence SEQ ID NO: 20 and a peptide of sequence comprising or consisting of a sequence having at least 80%, at least 85%, at least 90%, at least 95% of identity with SEQ ID NO: 20 over the entire length of SEQ ID NO: 20;

and/or of at least one expression vector comprising a nucleotide sequence encoding said at least one under the control of a promoter, which is effective in cells of said non-human animal; and b") collecting the resulting serum from said immunised non-human animal to obtain antibodies directed against said at least one peptide;

c") determining in vitro or ex vivo the ability of said antibodies obtained at said step b) to specifically bind the chemokine CXCL1, CXCL7, and CXCL8; and eventually d") selecting antibody(ies), which is (are) able to specifically bind the chemokines CXCL1, CXCL7 and CXCL8.

In particular step d") can comprise the selection of antibody(ies), which is (are) capable of binding to the human chemokine CXCL1 with an equilibrium dissociation constant ($K_D$) of at most 16 nM, to the human chemokine CXCL7 with an equilibrium dissociation constant ($K_D$) of at most 5 nM and to the human chemokine CXCL8 with an equilibrium dissociation constant ($K_D$) of at most 45 nM, as determined by surface plasmon resonance.

BRIEF DESCRIPTION OF DRAWINGS

FIG. 1(A-E) illustrates the capacity of the antibodies of the invention (produced by the two hybridomas CNCM I-4617 also designated by the inventors as 12A10-13 and CNCM I-4618 also designated by the inventors as 35B11-8) to inhibit tumor growth.

FIG. 1A: The peptide used for immunization is given (designated as pCXCL7). Comparison of this domain of CXCL7 with others domains of CXCL cytokines presenting the maximal similitude is also shown.

FIG. 1B: $3.10^6$ 786-O$^{LUC+}$ cells were subcutaneously injected into nude mice (n=10 per group). Fifteen days after injection, all mice developed tumors and were treated weekly with PBS for the control or with 15 mg/kg antibodies produced by the two hybridomas 12A10-13 or 35B11-8. Bioluminescence was measured weekly as described (Grepin et al., 2012). Data are the mean±SD. Statistical differences between the size of tumors of control and treated mice are presented: *p<0.05.

FIG. 1C: Average volume±SD and statistical analysis: *p<0.05; **p<0.01.

FIG. 1D: Representative images of the tumor-bearing mice.

FIG. 1E: The intra-tumor amounts of CXCL1, 7, 8 and VEGF were detected by ELISA. Data are the mean±SD. Statistical differences were *p<0.05; **p<0.011.

FIG. 4 represents the association and dissociation constant of the antibodies of the invention produced by the two hybridomas 12A10-13 (CNCM I-4617), 35B11-8 (CNCM I-4618) and commercially available antibodies (Pepotech®).

FIG. 5 represents the isotyping of the antibodies produced by the two hybridomas 12A10-13 (CNCM I-4617) and 35B11-8 (CNCM I-4618) antibodies. These antibodies were characterized as IgG2C for the antibodies produced by the hybridoma 12A10-13 and IgG1 for the antibodies produced by the hybridoma 35B11-8.

FIG. 7 show clinical and biological parameters and univariate analysis of patients.

FIG. 8 show clinical and biological parameters and multivariate analysis of patients FIGS. 9 (A-C) illustrate the effects of the antibodies of the invention produced by the two hybridomas 12A10-13 (CNCM I-4617) and 35B11-8 (CNCM I-4618) in a rat model of laser-induced choroidal neovascularization (ChNV). Choroidal neovascularization (ChNV) was induced using a 532 nm argon laser photocoagulator (six 75 μm-sized spots at 150 mW for 100 ms) in the right eyes of rats on Day O. The antibodies of the invention produced by the two hybridomas 12A10-13 (CNCM I-4617) (12A) and 35B11-8 (CNCM I-4618) (35B) were intravitreal administrated on Day O (30 μg/eye) as well as physiological serum as negative control (vehicule-VEH).

Figure 2:
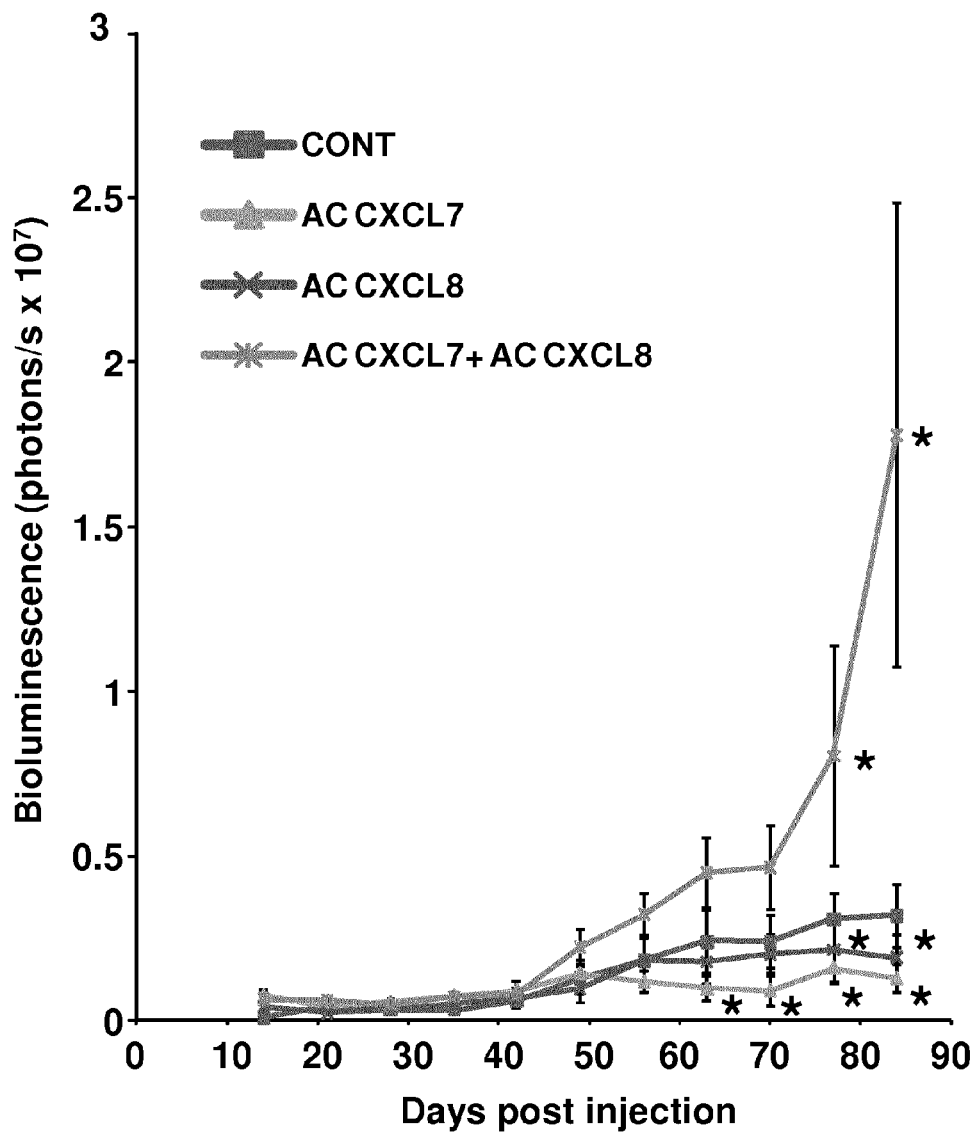
FIG. 2 illustrates the effects of commercially available antibodies directed against CXCL7 or CXCL8 on the growth of experimental ccRCC in nude mice. $3.10^6$ 786-O$^{LUC+}$ cells were subcutaneously injected into nude mice (n=7 per group). Fifteen days after injection, all mice developed tumors and were treated weekly with PBS for the control or with 15 mg/kg of commercially available anti-CXCL7 antibodies or of anti-CXCL8 antibodies (Prepotech® 500M33 and 500M08) or of the combination of both antibodies. Bioluminescence was measured weekly as described (Grepin et al., 2012). Statistical significant differences are shown: * p<0.05.
Figure 3:
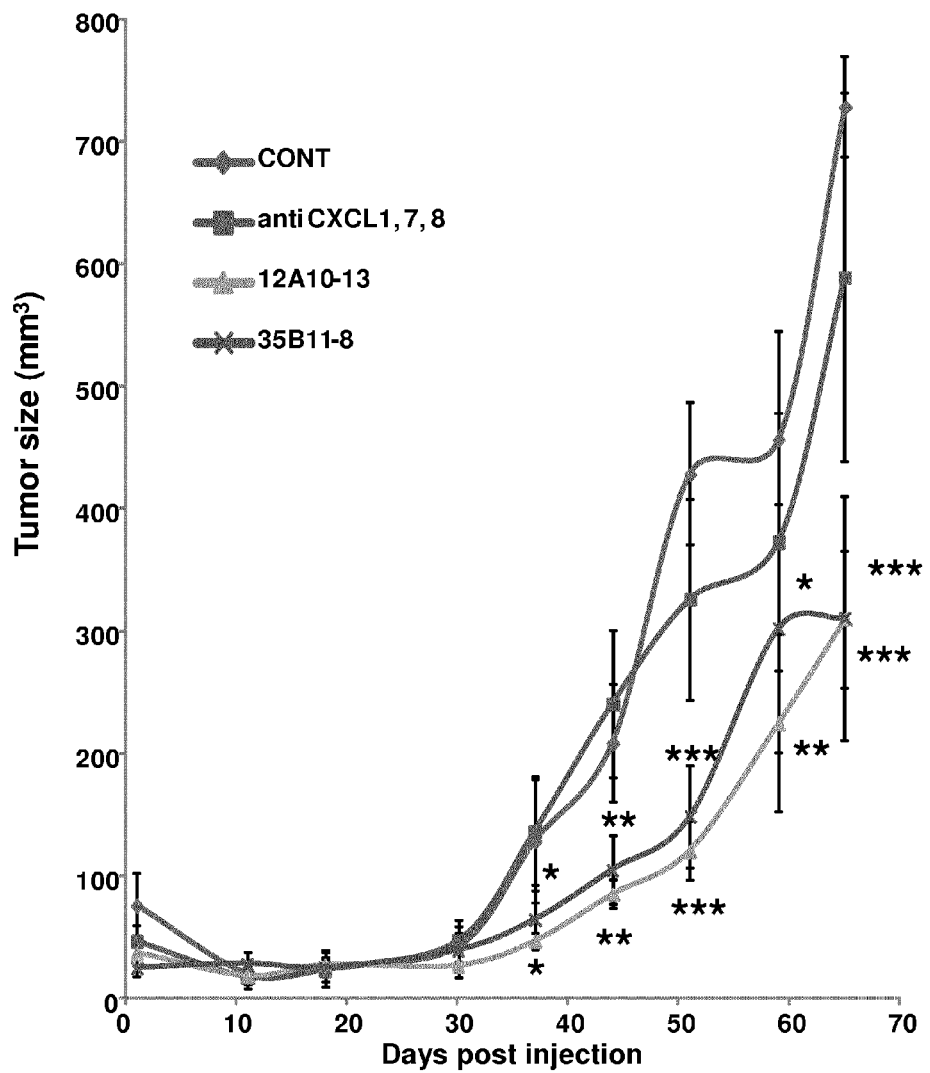
FIG. 3 illustrates the comparison of the effects of the combination of commercially available antibodies directed against CXCL1, CXCL7 or CXCL8 versus the effects of antibodies of the invention produced by the two hybridomas 12A10-13 (CNCM I-4617) and 35B11-8 (CNCM I-4618) on the growth of experimental ccRCC in nude mice. $3.10^6$ 786-O$^{LUC+}$ cells were subcutaneously injected into nude mice (n=10 per group). Fifteen days after injection, all mice developed tumors and were treated weekly with PBS for the control or with 15 mg/kg antibodies produced by the two hybridomas 12A10-13 or 35B11-8 or with 15 mg/kg of the combination of commercially available anti-CXCL1, anti-CXCL7 and CXCL8 antibodies (Prepotech® 500P92, 500M33 and 500M08). Tumor were measured with a caliper and the volume is calculated as the following (v=Lxl$^2$x0.52, Auerbach et al., 1978). Statistical significant differences are shown: * p<0.05;  p<0.01; * p<0.001.

The present invention will be explained in detail with examples in the following text, but the technical scope of the present invention is not limited to these examples.

EXAMPLES

I. Materials and Methods

Human Kidney Samples

The clinical characteristics of the patients and angiogenic profile of the normal and tumor tissues were described previously Grepin R, et al. (2012).

Cell Lines and Molecular Biology 786-O$^{LUC+}$, RCC-10$^{LUC+}$ and ACHN$^{LUC+}$ cells were obtained by lentiviral transduction (pLenti6/V5-D-TOPO, Invitrogen, France) and blasticidin selection (10 µg/ml).

Tumor Xenograft Formation and Size Evaluation

786-O$^{LUC+}$, RCC-10$^{LUC+}$ or ACHN$^{LUC+}$ cells (3.10$^6$ to 10.10$^6$ cells) were injected subcutaneously into the flanks of 5-week-old nude (nu/nu) female mice (Janvier, France). Bioluminescence was quantified using the In Vivo Imaging System (IVIS, Caliper LifeSciences, France) according to the manufacturer's instructions. Tumor volume (v=L×l$^2$× 0.52 (Auerbach et al., 1978)) was determined in parallel using a caliper. There was a linear relationship between values for bioluminescence and the tumor volume.

Measurement of Cytokines

CXCL cytokines, FGF, human and mouse VEGF were measured using PeproTech ELISA kits according to the manufacturer's recommendations (PeproTech, Neuilly-sur-Seine, France). VEGF-C was measured using the Human DuoSet ELISA kits, VEGF-D using the Quantikine ELISA Kit (R&D Systems, Minneapolis, USA).

Statistical Analysis

Statistical analyses were two-sided and were performed using R-2.12.2 for Windows. Statistical comparisons were performed using the Chi-2 test or Fisher exact test for qualitative data, the Student t-test or Wilcoxon test for quantitative data and the Log-Rank test for censored data.

Material and Methods Plasmon Resonance Analysis

Instrumentation

The surface Plasmon resonance biosensor, sold under the trademark BIACORE® 3000 SPR (surface Plasmon resonance), including a CM5 sensor chip, the control software 4.1 version, sold under the trademark BIACORE® 3000 control software 4.1 version and the BIAevaluation software 4.1 version (GE Healthcare).

Reagents

Amine coupling kit containing N-hydroxysuccinimide (NHS), N-ethyl-N'-(3-dimethylaminopropyl)-carbodiimide hydrochloride (EDC), and ethanolamine hydrochloride NaOH, pH8.5.

HBS-EP Buffer, an aqueous buffer containing 0.01 M HEPES, pH 7.4, 0.15 M NaCl, 3 mM EDTA, 0.05% (v/v) surfactant P20.

Mouse antibody capture kit containing the antibody capture (polyclonal rabbit anti mouse Immunoglobulin antibodies), the immobilisation buffer (10 mM sodium acetate pH5.0 solution) and the regeneration solution (10 mM glycine-HCl pH1.7 solution).

All these reagents are provided by GE Heathcare.

Antigen and Antibody

Polyclonal rabbit anti-Mouse IgG antibodies (Mouse antibody capture Kit, GE Healthcare), 1 mg/mL stock concentration.

Home made monoclonal rat IgG antibodies: Mc12A10-13 and Mc35B11-8, respectively 30.5 µg/µL and 32 µg/µL (stock concentration).

Commercial monoclonal mouse IgG antibodies: McCXCL1, McCXCL7, McCXCL8, McPan CXCL1-2-3. These antibodies are solubilized with filtered deionized water (mQ) to obtain respectively the following stock concentration of 2 mg/mL, 1 mg/mL, 1 mg/mL and 0.5 mg/mL.

The tested antigens are the cytokines CXCL1, CXCL3, NAP2, IL8, solubilised with filtered deionised to obtain the 1 mg/mL of stock concentration.

Immobilization of Capture Antibody on CM5 Sensor Chip Surface

The polyclonal rabbit anti mouse antibodies (Mouse antibody capture kit) are covalently immobilised on the CM5 sensor chip using standard amine coupling chemistry following the experimental protocol supplied by GE Healthcare.

First, the carboxymethyl dextran of the CM5 surface is activated with a 7 minutes injection of a 1:1 ratio of 0.4M EDC and 0.1M of NHS. Then the polyclonal rabbit anti mouse antibodies, diluted at 30 µg/mL in the immobilisation buffer (Mouse antibody capture kit), are immobilised on the activated surface with a 7 minutes injection. Remaining activated carboxymethyl dextran groups are blocked with a 7 minutes injection of 1M ethanolamine hydrochloride NaOH. This injection also removes the non-covalently bound antibodies.

These immobilisation steps are performed at 25° C., with a flow rate of 10 µL/min and with the HSP-EP running buffer.

With the surface plasmon resonance system, sold under the trademark BIACORE® 3000, 4 canals (Flow cell) are designed on the CM5 sensor surface. The polyclonal rabbit anti mouse IgG antibodies are covalently coupled on the 2$^{nd}$ 3$^{rd}$ and 4$^{th}$ flow cells (FC), leaving the first FC (FC1) blank for reference subtraction. The first FC (FC1) is only activated (EDC/NHS) and deactivated (ethanolamine hydrochloride NaOH), without injection of capture antibody.

Binding Analysis (Ligand Capture and Analyte Binding)

Binding analysis is performed using a wizard method especially "Binding using capturing molecule".

First the ligand (interest antibody) is captured by the immobilised antibodies. Diluted antibodies Mc12A10-13 (5 µg/mL), Mc35B11-8 (8 µg/mL), McCXCL1 (2 µg/mL), McCXCL7 (1 µg/mL), McCXCL8 (3 µg/mL), McPan CXCL1-2-3 (5 µg/mL) are captured by the polyclonal rabbit anti mouse IgG antibodies immobilised on the CM5 sensor chip with a 3 minutes injection at a flow rate of 5 µL/min. The complex "capture antibody—ligand" is stabilized during 10 minutes before the injection of the analyte (cytokines). This capture is a non-covalent interaction.

Then a range of cytokine concentration is injected (analyte) over the captured antibody (ligand). Cytokines CXCL1, CXCL3, NAP2, IL8 are injected over the captured ligand for a range of concentration from 0 to 10 µg/mL, at a flow rate of 20 µg/mL. The complex "ligand/analyte" is formed. The association and the dissociation phases are monitored over about 3 minutes and 2.5 minutes respectively. The signal induced is measured in RU (Resonance Unit).

A step of regeneration is performed between each cytokine (analyte) injection removing the complex "ligand-analyte". This step consists of an injection of regeneration buffer (Mouse antibody capture kit) at a flow rate of 20 µL/min. According to the tested "ligand-analyte" couple, the duration of the regeneration injection vary between 30 sec to 3 min. At the end of the regeneration step, the CM5 sensor chip is stabilized during 5 minutes minimum (5 to 7 minutes according to the tested "ligand-analyte" couple)

After the regeneration, only the capture antibody (polyclonal rabbit anti mouse IgG antibody) remains on the CM5 sensor chip. The chip is again ready for a new binding analysis cycle.

Antibodies and cytokines dilution are done with HBS-EP running buffer.

All these binding analysis are performed at 25° C. with the HBS-EP running buffer. Binding analysis is only monitored on the FC1 and FC2. As the FC1 is the control (blank), the signal measured in FC2 is subtracted by the signal obtained on the FC1. Furthermore, the signal obtained for each concentration of cytokine is subtracted by the signal obtained by running buffer injection (0 µg/mL of cytokine).

Material and Methods—Choroidal Neovascularization

Choroidal neovascularization (ChNV) was induced using a 532 nm argon laser photocoagulator (six 75 µm-sized spots at 150 mW for 100 ms) in the right eyes of rats on Day O.

Pigmented Brown Norway rats were divided into three groups of eight animals, each corresponding to three different treatments (intravitreal administration on Day O in the rat model of laser-induced choroidal neovascularization):
- 30 µg/eye of the antibodies of the invention produced by the hybridoma 12A10-13 (CNCM I-4617) (12A);
- 30 µg/eye of the antibodies of the invention produced by the hybridoma 35B11-8 (CNCM I-4618) (35B);
- Physiological serum as negative control (vehicle-VEH).

The size of the lesion was evaluated on Day 23 (post laser treatment).

Fundus neovessels were evaluated in the right eye on Days 14 and 21 by scoring lesion fluorescence intensity on angiograms (Heidelberg's Retinal Angiograph).

II. Results

II.1 Antibodies Directed Against CXCL1, CXCL7 and CXCL8 Decreased Tumor Growth

The protein sequence similarity of the ELR+CXCL was used in the development of antibodies that recognize concomitantly cytokines CXCL1, 7 and 8 involved in tumor growth.

For this purpose, the inventors immunized Lou/M rats with peptides specific for human CXCL7 of sequence SDLYAELRCMCIKTTSGIHPKNIQS (SEQ ID NO: 20). However, this peptide shared similarities with CXCL1, 2, 3 and 8 as shown FIG. 1A.

Different screening methods were used to isolate two different hybridomas 12A10-13 (CNCM I-4617), 35B11-8 (CNCM I-4618): ELISA tests on peptide of sequence SEQ ID NO: 20 coupled to keyhole limpet hemocyanine and the capacity of these antibodies to inhibit CXCL7-induced ERK activation in cells expressing CXCR2, as previously described (Bourcier C., et al. (2011)).

The equilibrium dissociation constant $K_D$ and the affinity constant Ka of these antibodies for the major CXCLs of interest was determined by plasmon resonance analysis, sold under the trademark BIACORE® Plasmon resonance analysis and are shown in FIG. 4. These results demonstrated multiple specificities of the two antibodies for different cytokines especially for CXCL7, CXCL1 and CXCL8. Moreover, the antibodies of the invention (produced by the two hybridomas 12A10-13/CNCM I-4617, 35B11-8/CNCM I-4618) are capable of binding to the human chemokine CXCL7 with a higher affinity than commercially available anti-CXCL7 antibodies.

These antibodies were characterized as IgG2C for the antibodies produced by the hybridoma 12A10-13 (CNCM I-4617) and IgG1 for the antibodies produced by the hybridoma 35B11-8 (CNCM I-4618) (FIG. 5). This characterization has been conducted using specific kits (Rat isotyping kit, AbD Serotec, reference: RMT1).

The capacity of the antibodies of the invention to inhibit tumor growth was evaluated by analysis of the effect of these antibodies on the development of ccRCC xenografted tumors in nude mice.

FIGS. 1B, C and D clearly show that both antibodies strongly inhibited tumor growth.

Moreover, both antibodies decreased the intra-tumor amounts of CXCL1, CXCL7 and CXCL8, the major cytokines implicated in tumor aggressiveness. Treatment of tumor-bearing mice with these antibodies also decreased VEGF expression, highlighting their strong anti-angiogenic effect (FIG. 1E).

These newly developed antibodies are able to inhibit tumor growth more efficiently than available commercial anti-CXCL1, anti-CXCL7 and anti-CXCL8 antibodies used alone or in combination (FIGS. 1B, 1C, 2 and 3). These results are really surprising since the combination of commercial anti-CXCL7 and anti-CXCL8 antibodies (with or without commercial anti-CXCL1 antibodies) does not able to obtain an additive effect on the inhibition of tumor growth. On the contrary, the inventors have shown that the combined use of commercial anti-CXCL7 and anti-CXCL8 antibodies is less efficient than their separate use on the inhibition of tumor growth and has a pro-tumoral effect in a mouse model of RCC (FIG. 2).

Figure 6:
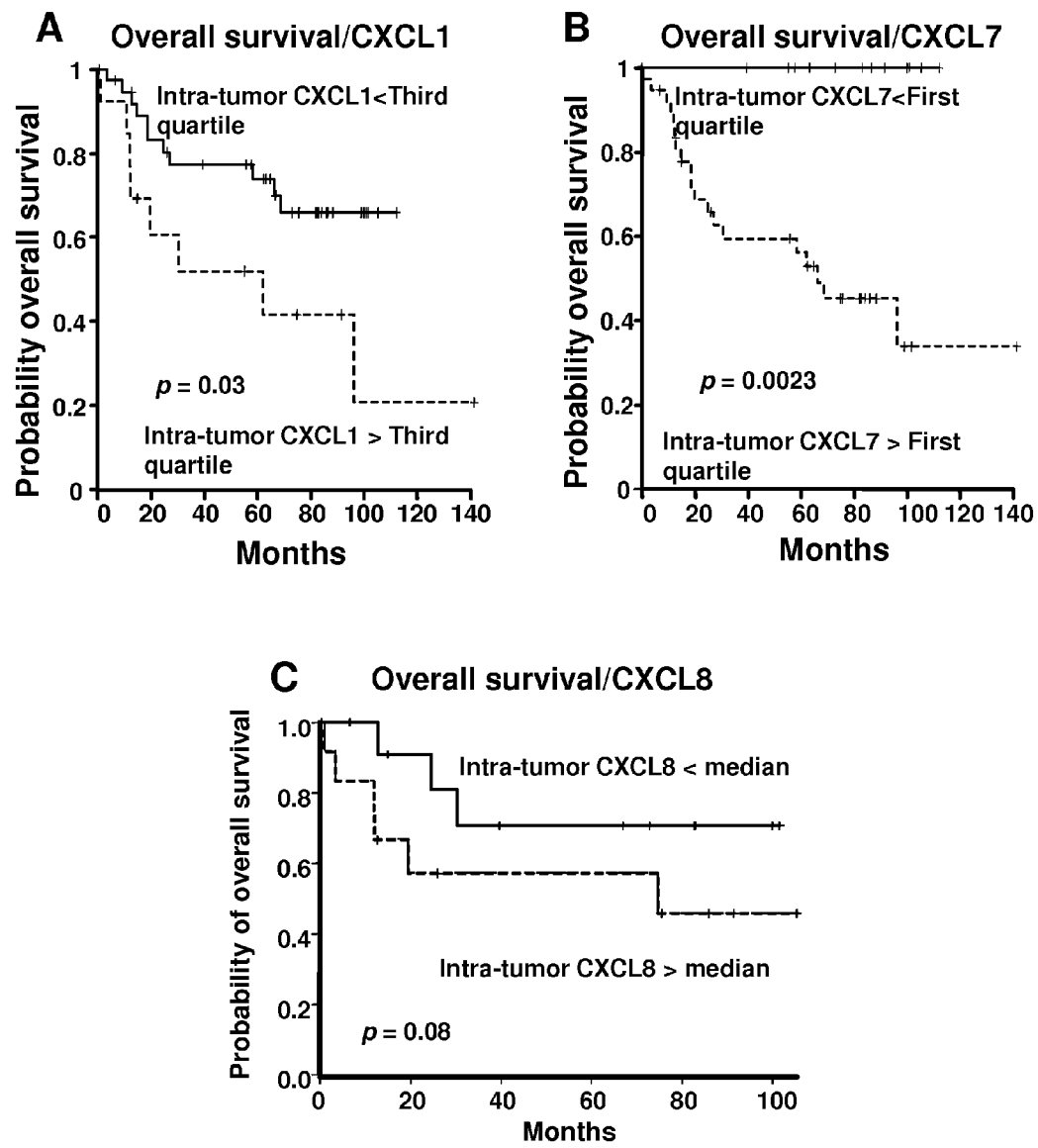
FIG. 6 represents Kaplan-Meier estimate of overall survival of patients with renal cell carcinoma. Correlation of overall survival with baseline levels of (FIG. 6 A) CXCL1 (third quartile value 96.2 pg/mg protein) and (FIG. 6 B) CXCL7 (first quartile value 1152 pg/mg protein) and (FIG. 6C) CXCL8 (median value 206 pg/mg). Overall survival was calculated from patient subgroups with baseline levels of CXCL1 that were less than or greater than the third quartile value or with baseline levels of CXCL7 that were less or greater than the first quartile value.

II.2 CXCL1, CXCL7 and CXCL8 are Prognostic Factor for Overall Survival of Clear Cell Renal Cell Carcinoma Patients To investigate whether chemokines CXCL1, CXCL7 and CXCL8 were associated with patient outcome, the correlation between the overall survival of 51 patients affected with clear cell renal cell carcinoma (ccRCC) (Grepin R, et al. (2012) and the intra-tumor amounts of the different chemokines were determined. In total, 22 patients (43%) died during the follow-up period. It is noteworthy that patients who exhibited CXCL1 levels superior to the third quartile (96.2 pg/mg) or CXCL7 levels superior to the first quartile (1152 pg/mg) had a significantly higher death rate (FIGS. 6A and B). Patients who exhibited CXCL8 levels superior to the median (206 pg/mg) had a higher death rate (FIG. 6C).

Univariate survival analysis showed that CXCL1 and CXCL7 expression was a factor of poor prognosis for overall survival (respectively p=0.017 and p=0.0015) (FIG. 7). Furthermore, metastasis at diagnosis and the Fürhman grade, which are both known to be poor prognostic factors for patient's outcome, also correlated significantly with overall survival (p=<$10^{-3}$ and 0.001).

The prognostic significance of the level of CXCL1, of CXCL7, of metastasis at diagnosis and of the Fürhman grade in terms of overall survival were then analyzed in a multivariate Cox regression model (FIG. 8). CXCL7 expression was identified as an independent prognostic parameter for overall survival (p=0.014) whereas CXCL1 did not reach statistical significance (p=0.059). Similar results were obtained for metastasis at diagnosis and the Fürhman grade with respect to overall survival (p=0.0005 and 0.007; FIG. 8).

These results show that the detection of overexpression of chemokines CXCL1, CXCL7 and CXCL8, in particular using the antibodies of the invention, is a prognostic factor for overall survival of patients affected with a pathological angiogenesis disease, clear cell renal cell carcinoma.

II.3 Antibodies Directed Against CXCL1, CXCL7 and CXCL8 Significantly Decreased Size Lesions and Reduced the Vascular Leakage in Rat Model of Laser-induced Choroidal Neovascularization To investigate the effect of antibodies directed against CXCL1, CXCL7 and CXCL8 in age-related macular degeneration, experiments were conducted on a rat model of laser-induced choroidal neovascularization.

Choroidal neovascularization (ChNV) was induced using a 532 nm argon laser in the right eyes of rats on Day O.

Pigmented Brown Norway rats were divided into three groups of eight animals, each corresponding to three different treatments (intravitreal administration on Day O in the rat model of laser-induced choroidal neovascularization):
    30 μg/eye of the antibodies of the invention produced by the hybridoma 12A10-13 (CNCM I-4617) (12A);
    30 μg/eye of the antibodies of the invention produced by the hybridoma 35B11-8 (CNCM I-4618) (35B);
    Physiological serum as negative control (vehicule-VEH).

Figure 9:
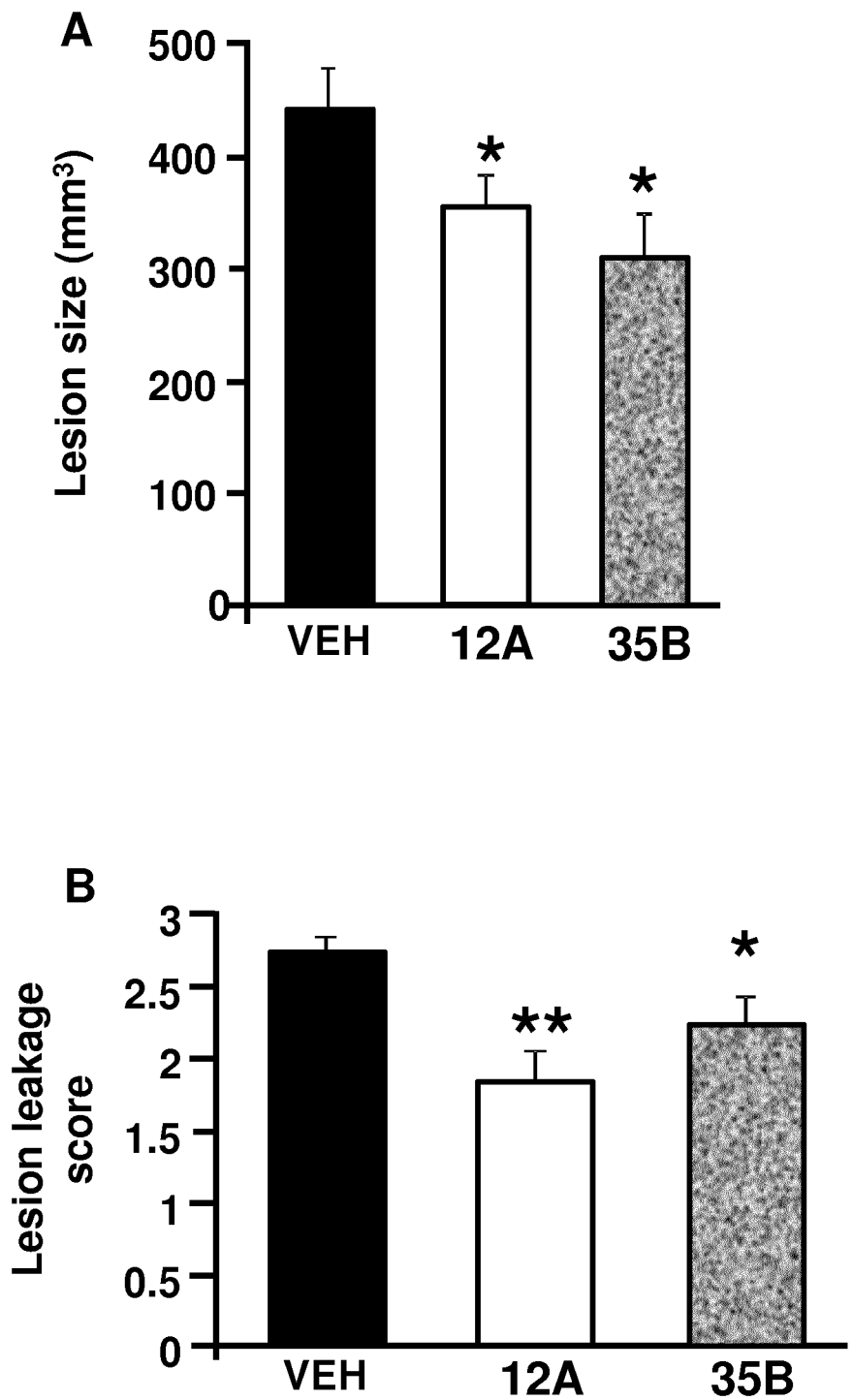
FIG. 9A represents the size of the lesion evaluation on Day 23 (post laser treatment). Data are the mean±SEM. Statistical analysis: * p<0.05.
FIG. 9B represents the angiographic evaluation on Day 14 (post laser treatment). Data are the mean±SEM. Statistical analysis: * p<0.05; **p<0.01. Fundus neovessels were evaluated in the right eye on Day 14 by scoring lesion fluorescence intensity on angiograms (Heidelberg's Retinal Angiograph).
FIG. 9C represents the angiographic evaluation on Day 21 (post laser treatment). Data are the mean±SEM. Statistical analysis: * p<0.05; **p<0.01. Fundus neovessels were evaluated in the right eye on Day 21 by scoring lesion fluorescence intensity on angiograms (Heidelberg's Retinal Angiograph).
Figure 9:
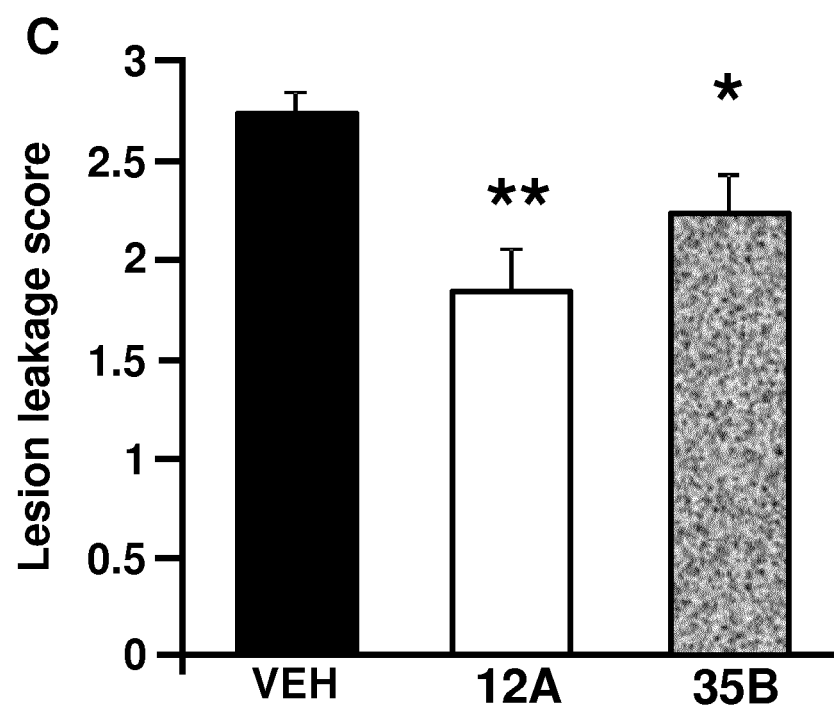

The size of the lesion was evaluated on Day 23 (post laser treatment). As shown on FIG. 9A, the size of the lesion was dramatically reduced on Day 23 after treatment by both the antibodies of the invention (12A10-13 (CNCM I-4617) (12A): p=0.0014; 35B11-8 (CNCM I-4618) (35B) p=0.004.

Fundus neovessels were evaluated in the right eye on Days 14 and 21 by scoring lesion fluorescence intensity on angiograms (Heidelberg's Retinal Angiograph). Results are shown on FIGS. 9B and 9C.

In the vehicle treated group (negative control-VEH), the induced eyes showed consistent fluorescein leakage 14 and 21 days after laser injury. The average fluorescein leakage was 2.8±0.2 (mean±SD, n=8, median=2.8) at Day 14 and 2.8±0.4 (mean±SD, n=8; median=3.0) at Day 21 with 78% of severe leaking spots (score 3), indicating the formation and the persistence of ChNV.

Intravitreal injection of 30 μg of the antibodies of the invention produced by the hybridoma 12A10-13 (CNCM I-4617) (12A) showed a 32% reduction of the vascular leakage on Days 14 and 21 in comparison with the vehicle group (p=0.002 and 0.0046, respectively), whereas a trend towards the suppression of leakage was observed in eyes injected with 30 μg of the antibodies of the invention produced by the hybridoma 35B11-8 (CNCM I-4618) (35B).

These results clearly show the efficiency of the antibodies of the invention to decrease size lesions and reduce the vascular leakage in rat model of laser-induced choroidal neovascularization.

BIBLIOGRAPHIC REFERENCES

Auerbach R, Morrissey L W, Sidky Y A. Regional differences in the incidence and growth of mouse tumors following intradermal or subcutaneous inoculation. Cancer Res. 1978;38:1739-44.
Bourcier C, et al. 2011. Constitutive ERK activity induces downregulation of tristetraprolin, a major protein controlling interleukin8/CXCL8 mRNA stability in melanoma cells. *Am J Physiol Cell Physiol* 301(3):C609-618.
Carmeliet P, Jain R K. 2000. Angiogenesis in cancer and other diseases. *Nature*. September 14;407 (6801):249-57.
Chothia C, Lesk A M. 1987. nonical structures for the hypervariable regions of immunoglobulins. J Mol Biol. August 20;196(4):901-17.
Chothia C, Lesk A M, Tramontano A, Levitt M, Smith-Gill S J, Air G, Sheriff S, Padlan E A, Davies D, Tulip W R, et al. Conformations of immunoglobulin hypervariable regions. Nature. December 21-28;342(6252):877-83. Review.
Choueiri T K, Plantade A, Elson P, Negrier S, Ravaud A, Oudard S, Zhou M, Rini B I, Bukowski R M, Escudier B. 2008 Efficacy of sunitinib and sorafenib in metastatic papillary and chromophobe renal cell carcinoma. J Clin Oncol. January 1;26(1):127-31.
Cole et al. 1986 Methods Enzymol, 121; 140-67
Ebos J M, Lee C R, Cruz-Munoz W, Bjarnason G A, Christensen J G, Kerbel R S. 2009.
Accelerated metastasis after short-term treatment with a potent inhibitor of tumor angiogenesis. Cancer Cell. March 3;15(3):232-9.
Eisen T, Oudard S, Szczylik C, Gravis G, Heinzer H, Middleton R, Cihon F, Anderson S, Shah S, Bukowski R, Escudier B; TARGET Study Group. 2008 Sorafenib for older patients with renal cell carcinoma: subset analysis from a randomized trial. J Natl Cancer Inst. October 15;100(20):1454-63.
Escudier B, Bellmunt J, Negrier S, Bajetta E, Melichar B, Bracarda S, Ravaud A, Golding S, Jethwa S, Sneller V. Phase III trial of bevacizumab plus interferon alfa-2a in patients with metastatic renal cell carcinoma (AVOREN): final analysis of overall survival. J Clin Oncol. 2010 May 1;28(13):2144-50. doi: 10.1200/JCO.2009.26.7849. Epub 2010 Apr. 5.
Grepin R, et al. (2012) Acceleration of clear cell renal cell carcinoma growth in mice following bevacizumab/Avastin treatment: the role of CXCL cytokines. *Oncogene* 31(13):1683-1694.
Harper S J, Bates D O. 2008 VEGF-A splicing: the key to anti-angiogenic therapeutics? Nat Rev Cancer; 8(11):880-7.
Hurwitz H, Fehrenbacher L, Novotny W, Cartwright T, Hainsworth J, Heim W, Berlin J, Baron A, Griffing S, Holmgren E, Ferrara N, Fyfe G, Rogers B, Ross R, Kabbinavar F. 2004 Bevacizumab plus irinotecan, fluorouracil, and leucovorin for metastatic colorectal cancer. N Engl J Med. June 3;350(23):2335-42.
Huse W D, Sastry L, Iverson S A, Kang A S, Alting-Mees M, Burton D R, Benkovic S J, Lerner R A. 1989. Generation of a large combinatorial library of the immunoglobulin repertoire in phage lambda. Science. December 8;246(4935):1275-81.
Köhler G, Milstein C. 1975Continuous cultures of fused cells secreting antibody of predefined specificity. Nature. August 7;256(5517):495-7.
Kozbor, D. & Roder, J. C. 1983. The production of monoclonal antibodies from human lymphocytes. Immunology Today, 4, 72-79.
Motzer R J, Escudier B, Oudard S, Hutson T E, Porta C, Bracarda S, Grunwald V, Thompson J A, Figlin R A, Hollaender N, Urbanowitz G, Berg W J, Kay A, Lebwohl D, Ravaud A; RECORD-1 Study Group. 2008 Efficacy of everolimus in advanced renal cell carcinoma: a double-blind, randomised, placebo-controlled phase III trial. Lancet. August 9;372(9637):449-56.
Pàez-Ribes M, Allen E, Hudock J, Takeda T, Okuyama H, Villals F, Inoue M, Bergers G, Hanahan D, Casanovas O.

2009 Antiangiogenic therapy elicits malignant progression of tumors to increased local invasion and distant metastasis. Cancer Cell. March 3;15(3):220-31.

Sambrook, Fritsch and Maniatis—"Molecular Cloning—A Laboratory Manual" Second Edition *Cold Spring Harbor Laboratory,* 1989.

Yao C, Lin Y, Ye C S, Bi J, Zhu Y F, Wang S M. 2007. Role of interleukin-8 in the progression of estrogen receptor-negative breast cancer. Chin Med J (Engl). October 20;120(20): 1766-72.

The invention claimed is:

1. An antibody and/or a fragment thereof, which is directed to the human chemokines CXCL1, CXCL7 and CXCL8, wherein light chain variable region ($V_L$) of the antibody comprises:
  a light chain CDR1 (LC-CDR1) of sequence SEQ ID NO: 1; and
  a light chain CDR2 (LC-CDR2) of sequence SEQ ID NO: 2; and
  a light chain CDR3 (LC-CDR3) of sequence SEQ ID NO: 3; and
wherein heavy chain variable region (VH) of the antibody comprises:
  a heavy chain CDR1 (HC-CDR1) of sequence SEQ ID NO: 4; and
  a heavy chain CDR2 (HC-CDR2) of sequence SEQ ID NO: 5; and
  a heavy chain CDR3 (HC-CDR3) of sequence SEQ ID NO: 6.

2. An antibody and/or a fragment thereof, which is directed to the human chemokines CXCL1, CXCL7 and CXCL8, wherein light chain variable region ($V_L$) of the antibody comprises:
  a light chain CDR1 (LC-CDR1) of sequence SEQ ID NO: 7; and
  a light chain CDR2 (LC-CDR2) of sequence SEQ ID NO: 8; and
  a light chain CDR3 (LC-CDR3) of sequence SEQ ID NO: 9; and
wherein heavy chain variable region ($V_H$) of the antibody comprises:
  a heavy chain CDR1 (HC-CDR1) of sequence SEQ ID NO: 10; and
  a heavy chain CDR2 (HC-CDR2) of sequence SEQ ID NO: 11; and
  a heavy chain CDR3 (HC-CDR3) of sequence SEQ ID NO: 12.

3. An antibody and/or a fragment thereof, which is directed to the human chemokines CXCL1, CXCL7 and CXCL8, wherein sequence of the light chain variable region ($V_L$) of the antibody comprises sequence SEQ ID NO: 13; and wherein sequence of the heavy chain variable region ($V_H$) of the antibody comprises sequence SEQ ID NO: 14.

4. An antibody and/or a fragment thereof, which is directed to the human chemokines CXCL1, CXCL7 and CXCL8, wherein sequence of the light chain variable region ($V_L$) of the antibody comprises sequence SEQ ID NO: 15; and wherein sequence of the heavy chain variable region ($V_H$) of the antibody comprises sequence SEQ ID NO: 16.

5. The antibody according to claim 1, 2, 3 or 4, wherein said antibody is a monoclonal antibody.

6. The antibody according to claim 3, said antibody being produced by the hybridoma under the deposit number CNCM I-4618.

7. The antibody according to claim 4, said antibody being produced by the hybridoma under the deposit number CNCM I-4617.

8. A nucleic acid molecule encoding an antibody or a fragment thereof as defined in claim 1, 2, 3, or 4.

9. A vector or a host cell comprising a nucleic acid molecule as defined in claim 8.

10. A pharmaceutical composition comprising a therapeutically effective amount of at least one compound selected from the group consisting of an antibody and/or a fragment thereof as defined in claim 1, 2, 3, or 4, nucleic acid molecule encoding an antibody and/or a fragment thereof as defined in claim 1, 2, 3, or 4 and a vector comprising a nucleic acid molecule encoding an antibody and/or a fragment thereof as defined in claim 2 3, 4 or 5, wherein the pharmaceutical composition is formulated in a pharmaceutical acceptable carrier.

* * * * *